(12) United States Patent
Bachar

(10) Patent No.: US 11,571,290 B2
(45) Date of Patent: Feb. 7, 2023

(54) UROLOGICAL IMPLANT HAVING EXTRACTION HANDLE AND/OR ARCHED MEMBERS

(71) Applicant: BUTTERFLY MEDICAL LTD., Yokneam (IL)

(72) Inventor: Yehuda Bachar, Givaat Shmuel (IL)

( * ) Notice: Subject to any disclaimer, the term of this patent is extended or adjusted under 35 U.S.C. 154(b) by 278 days.

(21) Appl. No.: 16/770,602

(22) PCT Filed: Dec. 3, 2018

(86) PCT No.: PCT/IL2018/051321
§ 371 (c)(1),
(2) Date: Jun. 7, 2020

(87) PCT Pub. No.: WO2019/111247
PCT Pub. Date: Jun. 13, 2019

(65) Prior Publication Data
US 2021/0161641 A1 Jun. 3, 2021

Related U.S. Application Data

(60) Provisional application No. 62/644,627, filed on Mar. 19, 2018, provisional application No. 62/595,147, filed on Dec. 6, 2017.

(51) Int. Cl.
*A61F 2/04* (2013.01)
*A61F 2/95* (2013.01)
*A61F 2/962* (2013.01)

(52) U.S. Cl.
CPC .............. *A61F 2/04* (2013.01); *A61F 2/9517* (2020.05); *A61F 2/962* (2013.01); *A61F 2002/048* (2013.01); *A61F 2002/9528* (2013.01)

(58) Field of Classification Search
CPC .......... A61F 2/04; A61F 2/9517; A61F 2/962; A61F 2002/048; A61F 2002/9528; A61F 2/86; A61F 2002/047; A61F 2230/0054
See application file for complete search history.

(56) References Cited

U.S. PATENT DOCUMENTS

| 5,269,802 A | 12/1993 | Garber |
| 2006/0276887 A1 | 12/2006 | Brady et al. |

(Continued)

FOREIGN PATENT DOCUMENTS

| WO | 2015111063 A1 | 7/2015 |
| WO | 2017017499 A1 | 2/2017 |

(Continued)

*Primary Examiner* — Jennifer Dieterle
*Assistant Examiner* — Rebecca Lynee Zimmerman

(57) ABSTRACT

Embodiments of a Urological implant include an implant with an elongated body having a longitudinal axis. Optionally longitudinal ribs symmetrically oppose each other and are connected to elongated body. The longitudinal ribs are optionally elastically shiftable between a collapsed state and an expanded state relative to the spinal longitudinal axis, in order to retract or/and support periurethral tissue. Optionally the system includes an implant extraction handle. The extraction handle is optionally positioned proximally to the elongated body and connected to the longitudinal rib and subject to a pulling force to facilitate and/or force approximation of the longitudinal supports to the longitudinal axis. In some embodiments, an implant body includes longitudinally spaced arched members, interconnected via arch ends sequentially along a length of a first and second longitudinal rib. Optionally the arched members are elastically bendable to facilitate elastic contractibility of the implant body under a transverse compressive force.

20 Claims, 18 Drawing Sheets

(56) References Cited

U.S. PATENT DOCUMENTS

| | | |
|---|---|---|
| 2008/0065209 A1 | 3/2008 | Pflueger |
| 2012/0136199 A1 | 5/2012 | Hou et al. |
| 2015/0257908 A1 | 9/2015 | Chao et al. |
| 2016/0317180 A1* | 11/2016 | Kilemnik .................. A61F 2/04 |
| 2017/0135830 A1* | 5/2017 | Harkin .................... A61F 2/848 |

FOREIGN PATENT DOCUMENTS

| | | |
|---|---|---|
| WO | 2018204883 A1 | 11/2018 |
| WO | 2019023633 A1 | 1/2019 |

* cited by examiner

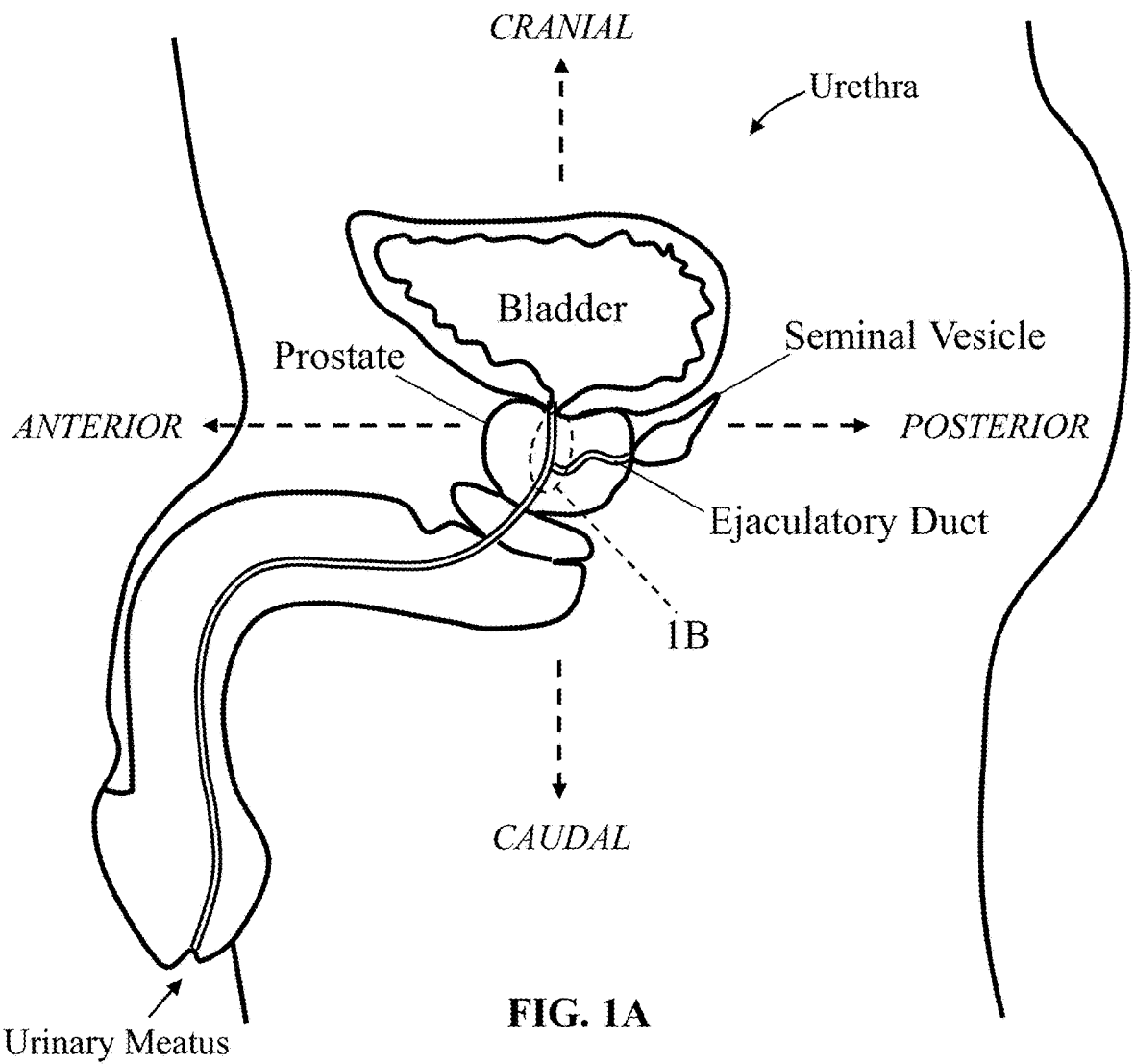
FIG. 1A
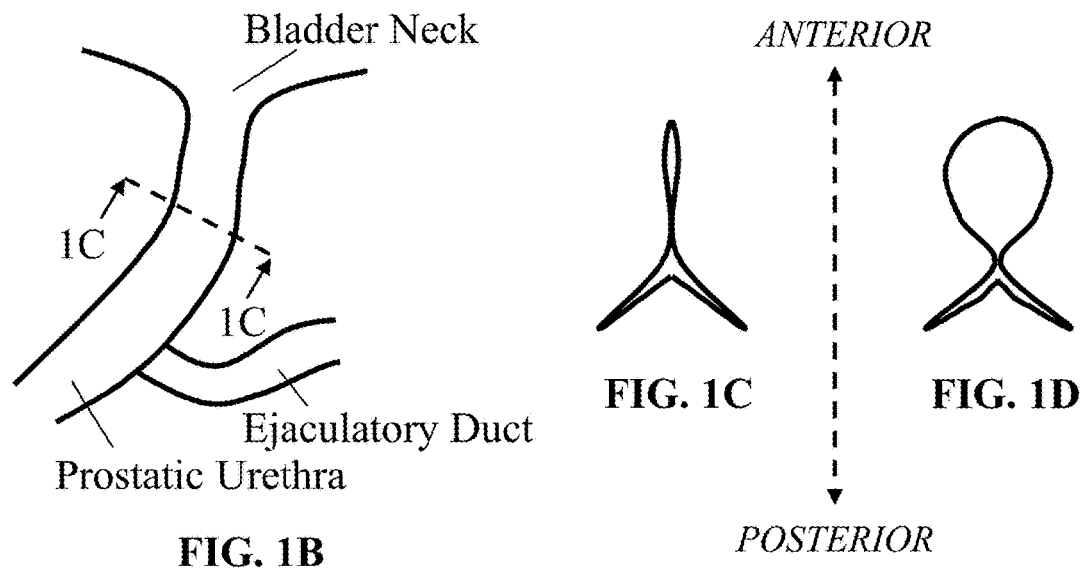
FIG. 1B
FIG. 1C
FIG. 1D

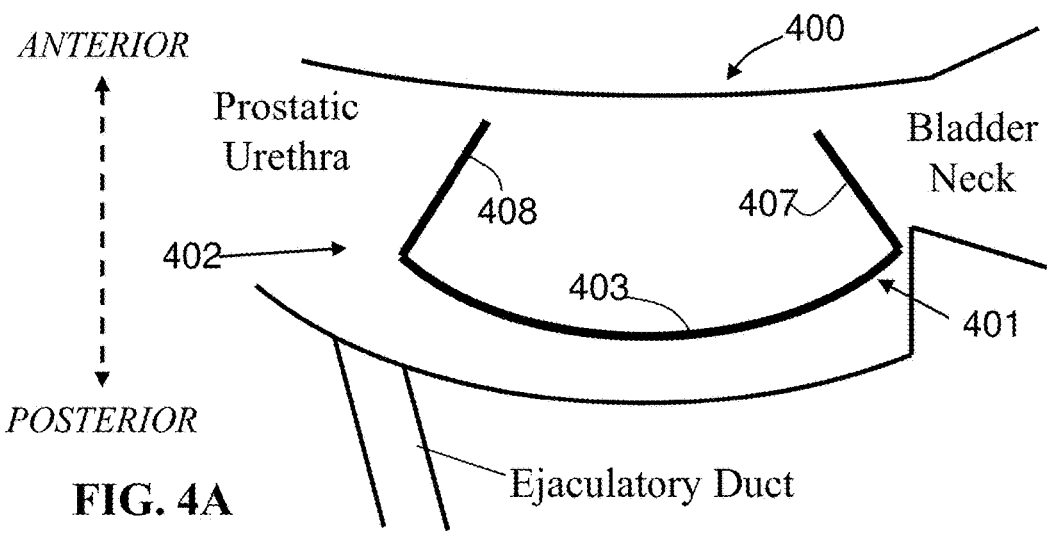
FIG. 4A
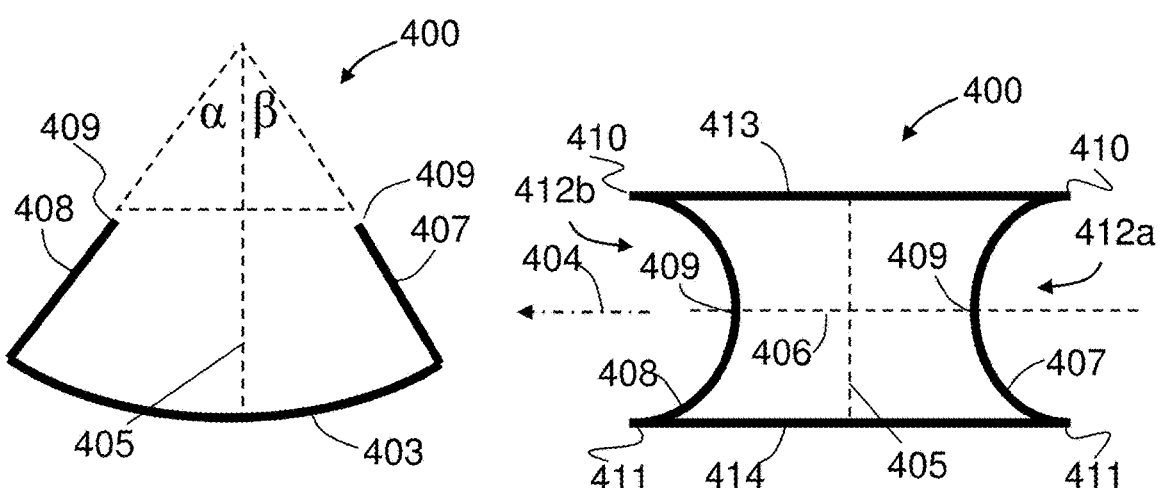
FIG. 4B
FIG. 4C
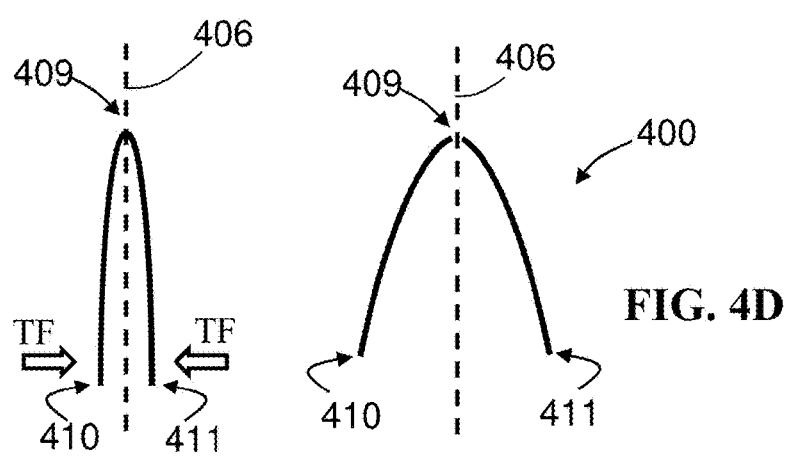
FIG. 4D

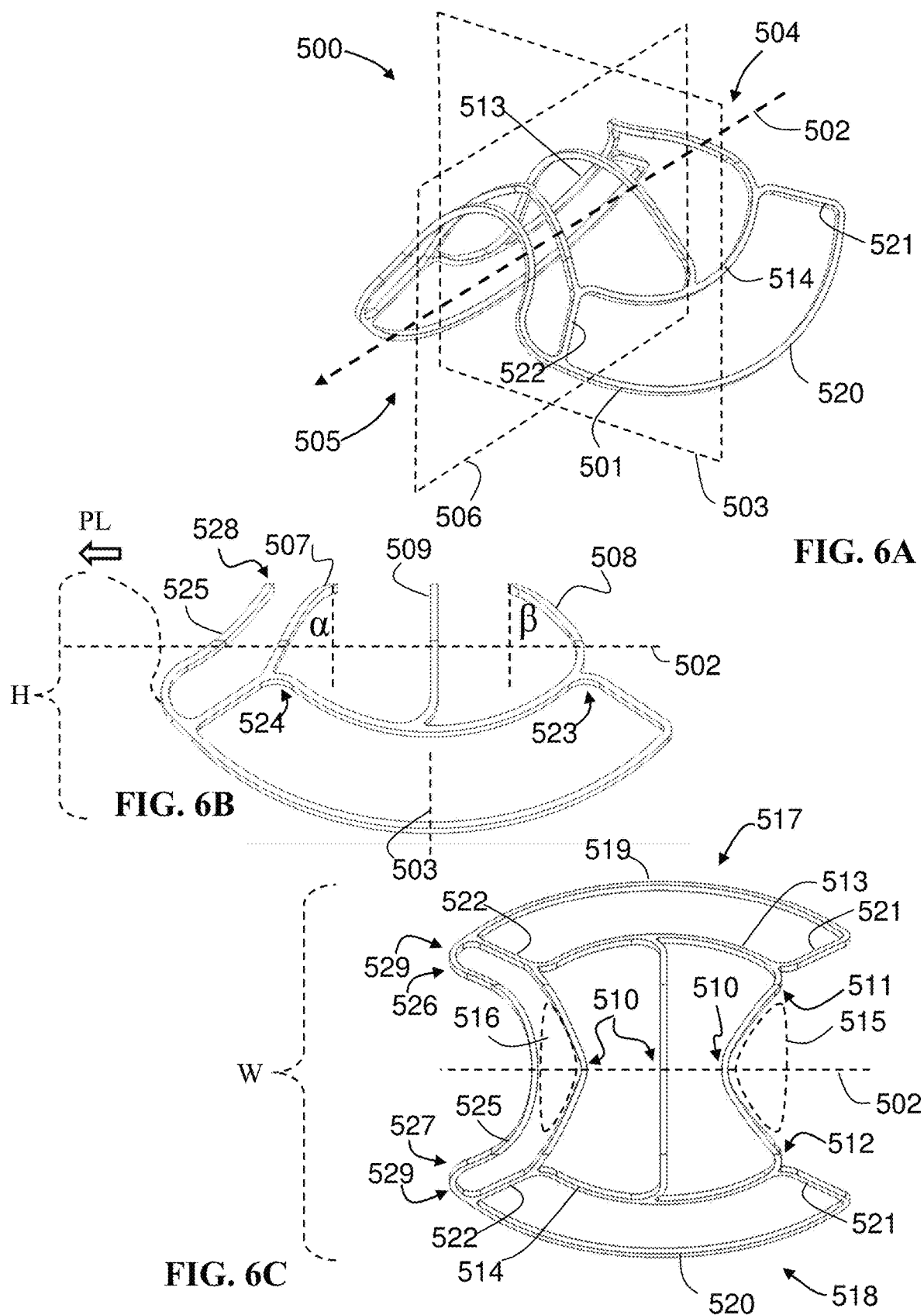

FIG. 14
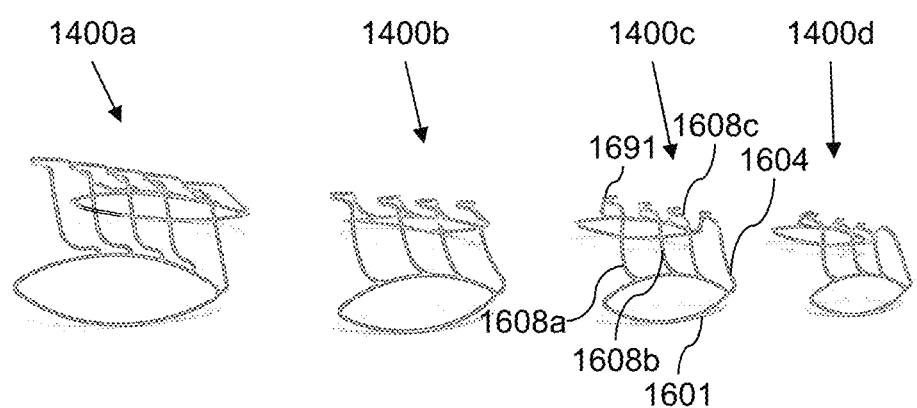
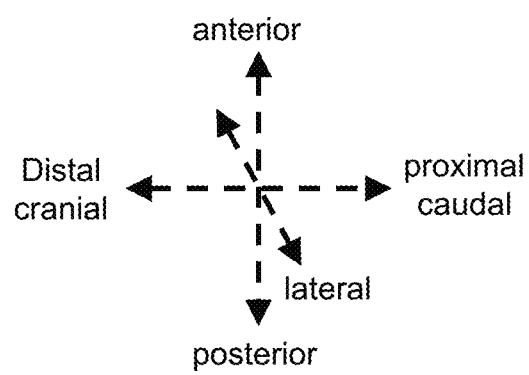

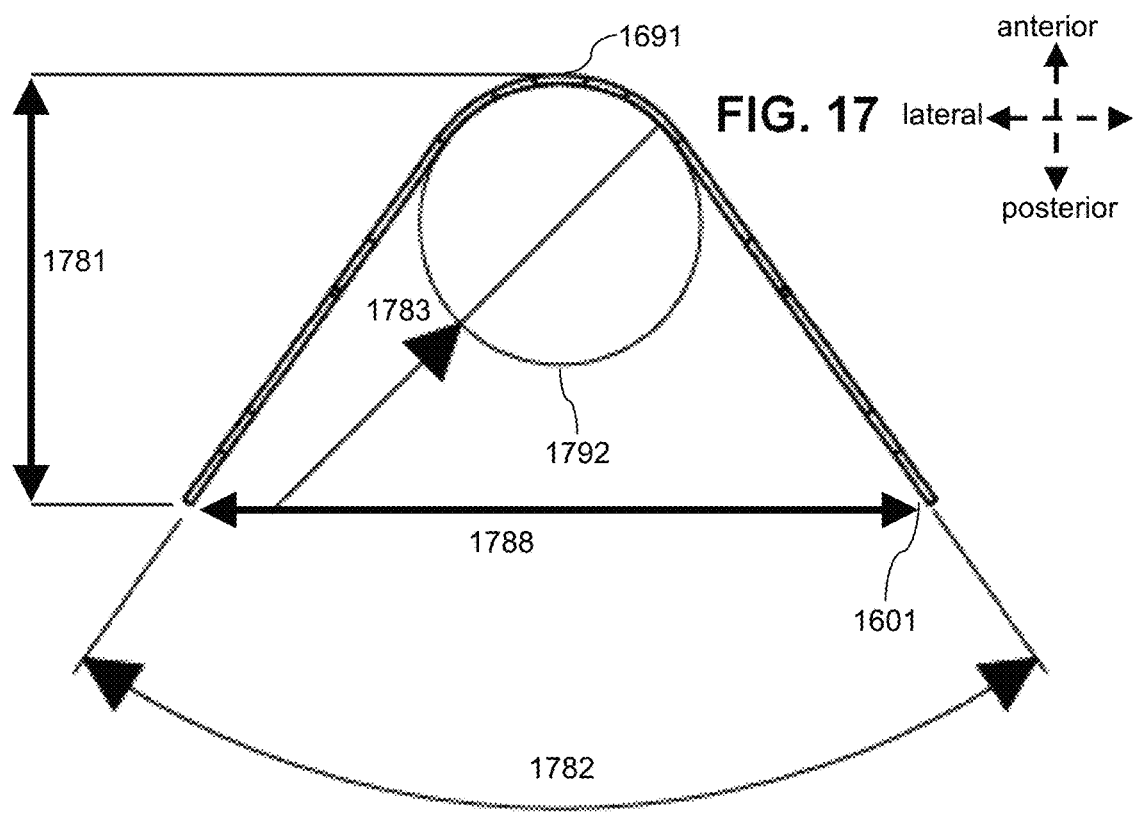
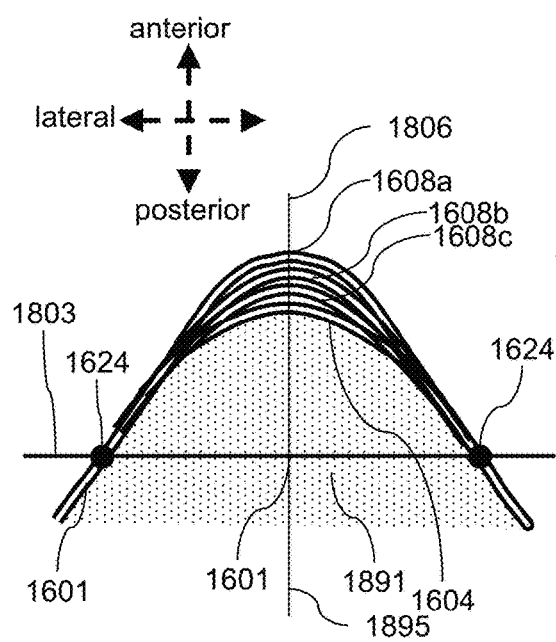
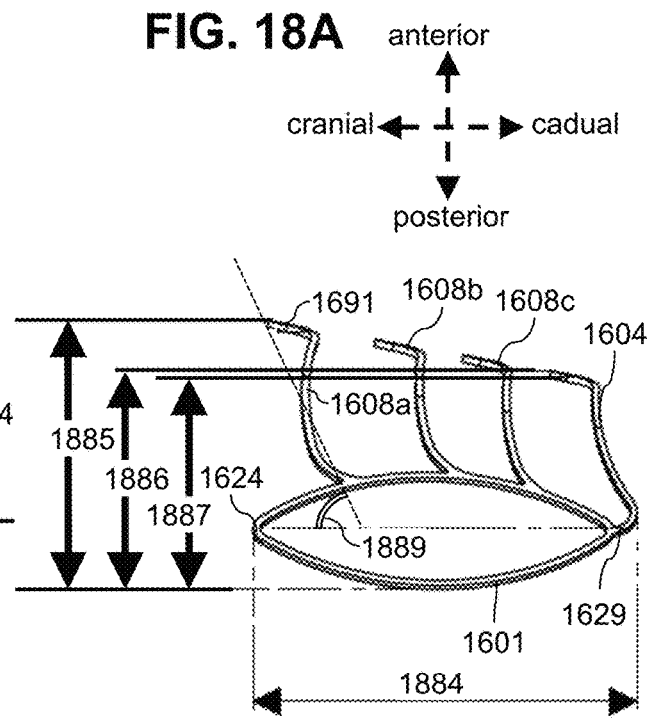

FIG. 22
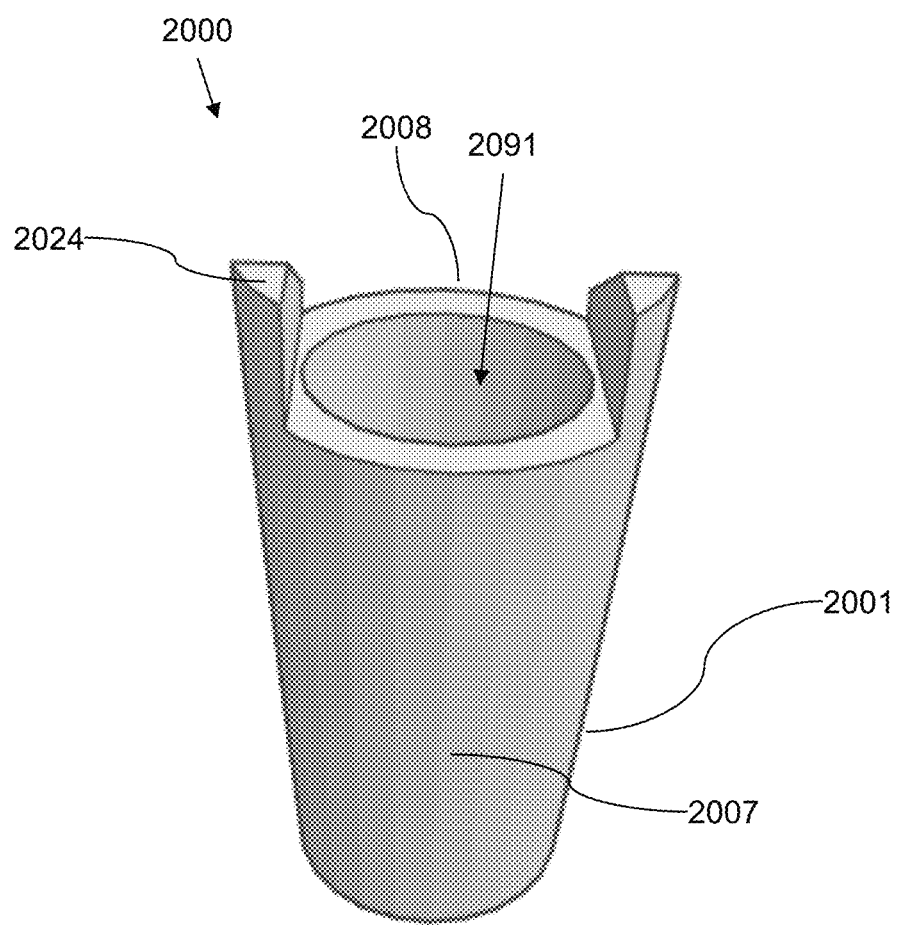
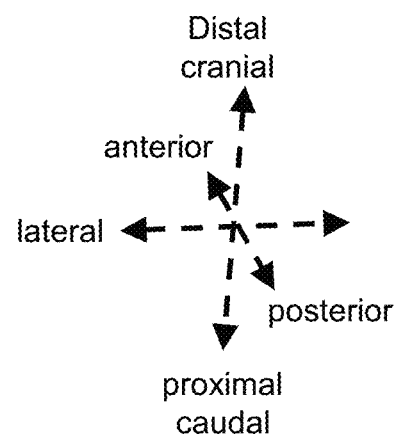

UROLOGICAL IMPLANT HAVING EXTRACTION HANDLE AND/OR ARCHED MEMBERS

RELATED APPLICATIONS

This application is a Continuation in part of PCT/IL2018/051321 filed Dec. 3, 2018 which claims priority of claims the benefit of priority under 35 USC § 119(e) of U.S. Provisional Patent Application No. 62/595,147 filed 6 Dec. 2017 and U.S. Provisional Patent Application No. 62/644,627 filed 19 Mar. 2018

This application in a continuation in part of U.S. patent application Ser. No. 16/403,632 filed May 6, 2019 which is a Continuation in part of U.S. patent application Ser. No. 15/747,940 filed Jan. 26, 2018 which is a Continuation-in-part of U.S. patent application Ser. No. 15/114,107 filed Jul. 26, 2016 which is a National Stage Entry of International application PCT/IB2015/055731 filed Jul. 29 2015 and is National Stage Entry of international application PCT/IL2015/050092 filed Jan. 26 2015 which Claims Priority from Provisional Application No. 61/931,645 filed Jan. 26, 2014

This application claims the benefit of priority under 35 USC § 119(e) of U.S. Provisional Patent Application No. 62/595,147 filed 6 Dec. 2017 and U.S. Provisional Patent Application No. 62/644,627 filed 19 Mar. 2018, and Provisional Application No. 61/931,645 filed Jan. 26, 2014 the contents of which are incorporated herein by reference in their entirety.

FIELD OF THE INVENTION

The present invention, in some embodiments thereof, relates to the field of urological medical devices and applications thereof, and more particularly, but not exclusively, to a urological (prostatic) implant, system, and method for retracting or/and supporting a prostatic urethra and/or periurethral tissue enclosing a prostatic urethra along a length of prostate lobes.

BACKGROUND OF THE INVENTION

Benign prostate hyperplasia (BPH), also known as benign prostatic hypertrophy, is a urological disease in which the prostate enlarges and constricts the urethra. BPH affects a majority of the male population over 50 years of age, and is thus of great medical and commercial importance.

Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). Surgical treatment is an invasive procedure that may be debilitating, painful and traumatic to the patient. Such surgical treatment may result in various complications including impotence, incontinence, bleeding, infection, and other undesirable problems.

Another procedure to treat prostatic hypertrophy is to place a catheter at the external opening of the urethra and into the obstructed portions of the urethra, allowing urine to pass from the bladder by way of the catheter lumen. These urinary catheters typically employ a positioning or retention balloon at the distal tip which inflates at the bladder neck and prevents the expulsion of the catheter from the body.

Ablation techniques based on using heat, such as produced by microwave or laser energy, may be provided in combination with such catheters for treating the enlarged portion of the prostate. However, such a procedure may result in pain and discomfort to the patient.

In spite of extensive teachings and practices in the field of urology, there is an on-going need for developing and practicing improved and new urological medical devices and applications thereof, for treating benign prostate hyperplasia (BPH).

SUMMARY OF THE INVENTION

The present invention, in some embodiments thereof, relates to a urological (prostatic) implant, system, and method for retracting or/and supporting periurethral tissue enclosing a prostatic urethra along a length of prostate lobes.

According to an aspect of some embodiments of the invention, there is provided an implant for retracting or/and supporting a prostatic urethra wall, the implant having an elongated implant body defining a longitudinal channel having a longitudinal axis, extending between a cranial end and a caudal end of the implant body; a pair of cranial projections configured to rest on a ledge of a bladder neck thereby preventing cranial drift of the implant into a bladder; a median plane including the longitudinal axis and perpendicular to a line connecting the cranial projections, the median plane having an anterior-posterior axis perpendicular to the longitudinal axis and wherein the line between the pair of cranial projections crosses the channel laterally on a posterior portion thereof.

According to some embodiments of the invention, a lateral width of a posterior portion of the channel is greater than a lateral width of an anterior portion of the channel.

According to some embodiments of the invention, the median plane divides the implant body into two symmetrical lateral halves.

According to some embodiments of the invention, the implant further includes a pair of posterolateral retractors; at least one cranial interconnecting member connecting a cranial portion of each of the pair of posterolateral retractors to a cranial anterior apex located on the median plane, wherein in an unstressed configuration the at least one cranial interconnecting member extends laterally and posteriorly from the cranial anterior apex to each of the posterolateral retractors; at least one caudal interconnecting member connecting a caudal portion of each of the pair of posterolateral retractors to a caudal anterior apex located on the median plane, wherein in an unstressed configuration the at least one caudal interconnecting member extends laterally and posteriorly from the caudal anterior apex to each of the posterolateral retractors; and wherein one of the pair of cranial projection projections projects in a cranial direction from each of the posterolateral retractors beyond the cranial interconnecting member.

According to some embodiments of the invention, in the unstressed configuration, a lateral width of the implant body between the pair of cranial projections is greater than a lateral width of the implant body between the caudal portions of the pair of posterolateral retractors.

According to some embodiments of the invention, the implant where a ratio of the width of the between the caudal portions of the pair of posterolateral retractors to the lateral width between the pair of cranial projections ranges between 9/10 to 6/10.

According to some embodiments of the invention, a height in an anterior direction of the cranial apex from the cranial portion of the posterolateral retractors is greater than a height in the anterior direction of the caudal apex from the caudal portion of the posterolateral retractors.

According to some embodiments of the invention, each of the at least one cranial connecting member and the at least one caudal connecting member is elastically bendable so as to facilitate elastic contractibility of the implant body when the implant body is subjected to a transverse compressive force crossing the median plane.

According to some embodiments of the invention, a ratio of a length of the implant in a longitudinal direction and an average anterior height of the cranial apex and the caudal apex from the pair of posterolateral retractors ranges between 12/10 to 16/10.

According to some embodiments of the invention, the implant further includes: wherein the at least one caudal connecting member is configured to shift elastically, under a pulling force away from the at least one cranial connecting member to facilitate approximation of the pair of posterolateral retractors relative to the longitudinal axis.

According to some embodiments of the invention, the implant body has a total height in an anterior posterior direction within a range of 10 mm to 40 mm and a width in a lateral direction within a range of 8 mm to 30 mm, when in an expanded configuration.

According to some embodiments of the invention, a posterior side of the implant body is open.

According to an aspect of some embodiments of the invention, there is provided a set of implants for a prostatic urethra including: a large implant having an elongated implant body having a longitudinal axis, the longitudinal axis extends between a cranial end and a caudal end of the implant body along a median plane dividing the implant body into two symmetrical halves the median plane having an anterior-posterior axis perpendicular to the longitudinal axis is perpendicular to a transverse plane and, the transverse plane having lateral axis perpendicular to the an anterior-posterior axis and perpendicular to the longitudinal axis; a pair of posterolateral retractors; a small implant proportionally similar within 10% to the large implant.

According to some embodiments of the invention, in an unstressed configuration, a lateral width of a cranial end portion of the implant body is greater than a lateral width of a caudal end portion of the implant body.

According to some embodiments of the invention, the set where a ratio of the width of a caudal end portion and the lateral width of a cranial end portions ranges between 9/10 to 6/10.

According to some embodiments of the invention, a height in an anterior direction of a cranial end portion of the implant body is greater than a height in the anterior direction of a caudal end portion of the implant body.

According to some embodiments of the invention, a ratio the height in the anterior direction of the cranial portion to the height in the anterior direction of the caudal end portion ranges between 11/10 to 14/10.

According to some embodiments of the invention, each implant body is elastically bendable so as to facilitate elastic contractibility of the implant body when the implant body is subjected to a transverse compressive force crossing the median plane.

According to some embodiments of the invention, the large implant has a total height in an anterior posterior direction within a range of 30 mm to 40 mm and a width in a lateral direction within a range of 22 mm to 30 mm, when in an expanded configuration and the small implant has a total height in the anterior posterior direction within a range of 10 mm to 13 mm and a width in the lateral direction within a range of 8 mm to 11 mm, when in an expanded configuration.

According to some embodiments of the invention, a posterior side of the implant body is open.

According to an aspect of some embodiments of the invention, there is provided a urological implant, including: an connecting member; a first longitudinal rib and a second longitudinal rib symmetrically opposing each other and elastically shiftable away from each other between a collapsed state and an expanded state, relative to a longitudinal axis of the implant; the expanded state for retracting or/and supporting periurethral tissue enclosing a prostatic urethra; and an implant extraction handle connected at one side thereof to the first longitudinal rib and at second side thereof to the second longitudinal rib, wherein the extraction handle is configured to shift elastically, under a pulling force away from the connecting member to facilitate and/or force approximation of the first and second longitudinal ribs relative to the longitudinal axis.

According to some embodiments of the invention, the connecting member includes at least one arched member connecting at one end thereof to the first longitudinal rib and on a send end thereof to the second longitudinal rib.

According to some embodiments of the invention, the arched member is inclined distally in the expanded state.

According to some embodiments of the invention, implant is configured to collapse to an insertion configuration fitting into a urinary catheter wherein the handle is collapsed distally.

According to some embodiments of the invention, implant is configured to collapse to an extraction configuration fitting into a urinary catheter wherein the handle is collapsed proximally.

According to some embodiments of the invention, a distal end of the connecting member is configured to remain proximal to a distal end of the rib in the expanded state.

According to some embodiments of the invention, a distal end of the connecting member is configured to remain proximal to a distal end of the rib in the collapsed state.

According to an aspect of some embodiments of the invention, there is provided a urological implant having extraction handle. Optionally, the implant has an elongated implant body having a longitudinal axis and two or more longitudinal ribs elastically shiftable away from each other between a collapsed state and an expanded state, relative to the longitudinal axis. Optionally, the device may be biased to the expanded state. For example, the device may be configured for supporting periurethral tissue enclosing a prostatic urethra in the expanded state. Optionally, in the collapsed state the device may be inserted and/or extracted from the urethra (for example using a sheath and/or a catheter for example the sheath may have an internal diameter between 2 to 4 mm and/or between 4 to 6 mm and/or between 6 to 10 mm), for example the device may collapse to a width of between 2 to 4 mm and/or 4 to 6 mm and/or between 6 to 8 mm and/or between 8 to 10 mm. In some embodiments, pulling implant extraction handle proximally urges the device toward the collapsed state.

In some embodiments, the extraction handle is attached to the implant body, for example to a proximal portion thereof. Optionally, one side of the longitudinal rib is connected at to a first longitudinal rib and at second side thereof to a second longitudinal rib. Optionally, the extraction handle is configured to shift elastically, under a pulling force away from the implant body to facilitate and/or force approximation of the first and second longitudinal ribs relative to the longitudinal axis.

In some embodiments, the longitudinal ribs are interconnected by a connecting member. For example, the connecting member may include a longitudinal spine and/or one or more arched members. Optionally the first and second longitudinal ribs symmetrically oppose each other. Optionally, the device is in the expanded state when the connecting member is in a relaxed state and/or the device body forces the longitudinal ribs outward as the device collapses towards the collapsed state.

Some embodiments are further characterized in that the implant extraction handle is shaped to correspond to an outline of the urological implant at a proximal end thereof in the expanded relaxed state.

Some embodiments are further characterized in that the extraction handle includes an apex.

Some embodiments are further characterized in that the apex is centered between the first and second longitudinal ribs.

Some embodiments are further characterized in that in the relaxed state the apex is adjacent to a proximal end of the implant body and the pulling causes the apex to move in a proximal direction away from the implant body proximal end.

Some embodiments are further characterized in that the implant extraction handle is symmetrically connected to the first and second longitudinal ribs.

According to an aspect of some embodiments of the present invention, there is provided a urological implant, comprising:

an elongated implant body having a longitudinal axis;

a first longitudinal rib and a second longitudinal rib symmetrically opposing each other and connected to the implant body, and elastically shiftable away from each other between a collapsed state and a relaxed state, relative to the longitudinal axis, for retracting or/and supporting periurethral tissue enclosing a prostatic urethra; and an implant extraction handle provided proximally distant to the implant body and symmetrically connected at one side thereof to the first longitudinal rib and at second side thereof to the second longitudinal rib.

In some embodiments, the implant extraction handle is shaped to correspond an outline of the urological implant formed by the first and second longitudinal ribs with an extraction handle apex thereof provided adjacent a proximal end of the implant body, In some embodiments, the implant extraction handle is configured to shift elastically, when under a pulling force originating therefrom, such that the extraction handle apex points in a proximal direction towards and/or along the longitudinal axis and away from the implant body proximal end, so as to facilitate and/or force approximation of the first and second longitudinal ribs relative to the longitudinal axis.

In some embodiments, the implant body includes a spine member.

In some embodiments, the implant extraction handle configured to recollapse the first and second longitudinal ribs into the collapsed state, when the urological implant is pulled proximally from the implant extraction handle against an edge of a retraction sheath enclosing a lumen sized to accommodate the urological implant therein when in the collapsed state.

In some embodiments, each the first and second longitudinal ribs includes a proximally projecting lateral corner and a distally projecting lateral corner, relative to the longitudinal axis, and the implant extraction handle is connected to the first and second longitudinal ribs at the proximally projecting lateral corners thereof so as to facilitate forcing of the proximally projecting lateral corners to approximate each other when the urological implant is pulled proximally from the implant extraction handle against the sheath edge.

In some embodiments, each the first and second longitudinal ribs is curved and includes a proximal rib end joined to a proximal end of the spine member, a distal rib end joined to a distal end of the spine member, and an elongated rib edge portion provided between the proximal and distal corresponding rib ends that is sized and shaped for positioning in a corresponding posterolateral interlobar groove, when the spine member is positioned in and along an anterior interlobar groove in the prostatic urethra.

According to an aspect of some embodiments of the present invention, there is provided a method for extracting the urological implant, comprising:

positioning the edge of the extraction sheath in the prostatic urethra;

applying a fastener to emerge from the extraction sheath distally into the prostatic urethra and to fasten onto a mid-portion of the implant extraction handle; and pulling the urological implant proximally from the implant extraction handle against the sheath edge, thereby recollapsing the urological implant until reaching the collapsed state and further withdrawing the urological implant into the extraction sheath lumen.

In some embodiments, pulling the urological implant deforms the implant extraction handle such that deformation stresses developed thereinside force the first and second longitudinal ribs to approximate one to other until reaching the collapsed state.

In an aspect of some embodiments of the present invention, there is provided a urological implant for retracting or/and supporting a prostatic urethra wall. The implant comprising an elongated implant body having a longitudinal axis, the longitudinal axis is perpendicular to a transverse plane and extending between a cranial end and a caudal end of the implant body along a median plane. Optionally the longitudinal axis divides the implant body into two symmetrical halves.

In some embodiments, the implant body includes longitudinally spaced arched members, each of the arched members includes an unsupported arch apex located between a first arch end and a second arch end, forming together an arched member plane being perpendicular to the median plane.

In some embodiments, the arched members are interconnected via arch ends thereof. For example, the first arch ends of the arched members may be connected sequentially along a length of a first longitudinal rib portion, and/or the second arch ends of the arched members may be connected sequentially along a length of a second longitudinal rib portion. Optionally, each of the first and second longitudinal rib portions extends through the transverse plane;

In some embodiments, each one of the arched members is elastically bendable so as to facilitate elastic contractibility of the implant body when the implant body is subjected to a transverse compressive force crossing the median plane.

In some embodiments, the implant body is sized and configured to retract or/and support an anterior portion of the prostatic urethra wall, and allowing collapse of an unsupported posterior portion of the prostatic urethra wall opposing the anterior portion.

In some embodiments, the implant body further includes a first lateral spacer emerging from the first longitudinal rib and a second lateral spacer emerging from the second longitudinal rib, being independently contractible when subjected to a sagittal compressive force parallel to the median plane.

In an aspect of some embodiments of the present invention, there is provided a method for supporting or/and extracting a wall of a partially constricted prostatic urethra, the method comprising:

providing the urological implant;

positioning the implant in the partially constricted prostatic urethra with the implant body contracted into a chosen contracted size and shape configured for atraumatic insertion in the partially constricted prostatic urethra, wherein each the arch apex is located adjacent midline of an anterior portion of the prostatic urethra wall;

releasing the implant body thereby allowing the arched members to autonomously shift the first and second longitudinal rib portions away from each other relative to the median plane, to contact the wall of the partially constricted prostatic urethra and to retract the prostatic urethra by pressing against the prostatic urethra wall.

All technical or/and scientific words, terms, or/and phrases, used herein have the same or similar meaning as commonly understood by one of ordinary skill in the art to which the invention pertains, unless otherwise specifically defined or stated herein. Methods, materials, and examples described herein are illustrative only and are not intended to be necessarily limiting. Although methods or/and materials equivalent or similar to those described herein can be used in practicing or/and testing embodiments of the invention, exemplary methods or/and materials are described below. In case of conflict, the patent specification, including definitions, will control.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using a computerized operating system.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIGS. 1A-1D schematically illustrate cross sectional views of a male urethra shown in a constricted state (FIG. 1C) and in a patent state (FIG. 1D), in accordance with some embodiments of the invention;

FIGS. 4A-4D schematically illustrate views of an exemplary urological implant having two spaced arches, in accordance with some embodiments of the invention;

FIGS. 6A-6C illustrate views of an exemplary urological implant having three spaced arches, two lateral spacers and an extraction handle, in accordance with some embodiments of the invention;

FIG. 14 illustrates 4 sizes of implants a large implant 1400*a*, a medium-large implant 1400*b*, a medium implant 1400*c* and a small implant 1400*d* in accordance with embodiments of the current invention;

FIG. 17 illustrates folding of an implant in accordance with an embodiment of the current invention;

FIG. 18A is a lateral orthogonal view of an implant in accordance with In some embodiments of the current invention;

FIG. 18B is an axial view of an implant in accordance with an embodiment of the current invention;

FIG. 22 is a posterior cranial view of a tapered tubular implant in accordance with an embodiment of the current invention.

DESCRIPTION OF SPECIFIC EMBODIMENTS OF THE INVENTION

The present invention, in some embodiments thereof, relates to the field of urological medical devices and applications thereof, and more particularly, but not exclusively, to a urological (prostatic) implant, system, and method for retracting or/and supporting a wall of a prostatic urethra and/or periurethral tissue enclosing a prostatic urethra along a length of prostate lobes.

FIGS. 1A-1D schematically illustrate cross sectional views of a male urethra. FIG. 1B is a magnification of the body portion containing the prostatic urethra. The urethra connects the urinary bladder to the urinary meatus for the removal of urine and semen from the body. Furthermore, the prostatic urethra merges about mid length thereof with an ejaculatory duct for carrying semen therein from the seminal vesicle. The prostatic urethra begins at the bladder neck and runs through the prostate approximately 3 cm in length. It begins almost vertically (in a caudal direction) from the bladder then curved anteriorly. In view thereof, inventor believes a urological implant having a curved body mimicking prostatic urethra curvature is advantageous for both immediate implantation phase, and for long term presence in the prostatic urethra, so as to physically effect and maintain a healthy and patent prostatic urethra.

FIGS. 1C-1D illustrate a cross section of the prostatic urethra along line '1C:1C'. FIG. 1C shows the prostatic urethra in a constricted state, whereas a normal state would be more similar to a trefoil (three-lobed) shape. FIG. 1D, on the other hand, illustrates a patent, partially opened, state with an anterior lobe fully opened, yet the two posterior lobes substantially closed. The patent state shown in FIG. 1D is considered by the inventor of the present invention as having advantages even with respect to the natural fully opened state, since that it suppresses retrograde (cranial) flow towards the urine bladder the of semen arriving at the posterior portion of the prostatic urethra via the ejaculatory duct.

Figure 1E:
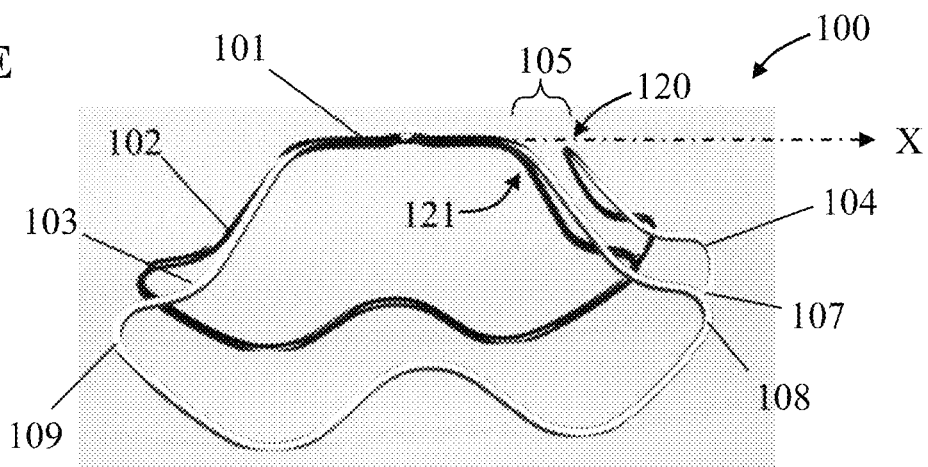
FIGS. 1E-1F show views of an exemplary urological implant comprising an implant extraction handle, in accordance with some embodiments of the invention.
Figure 1F:
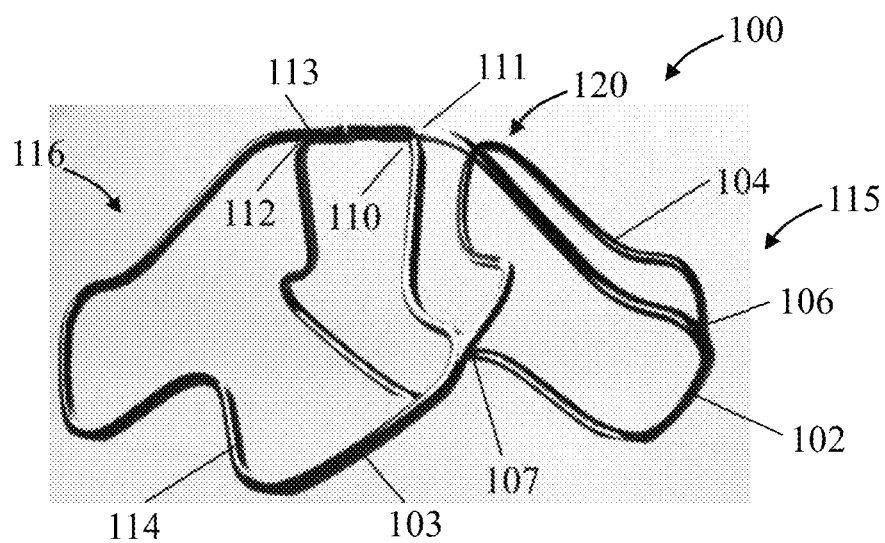
Figure 2:
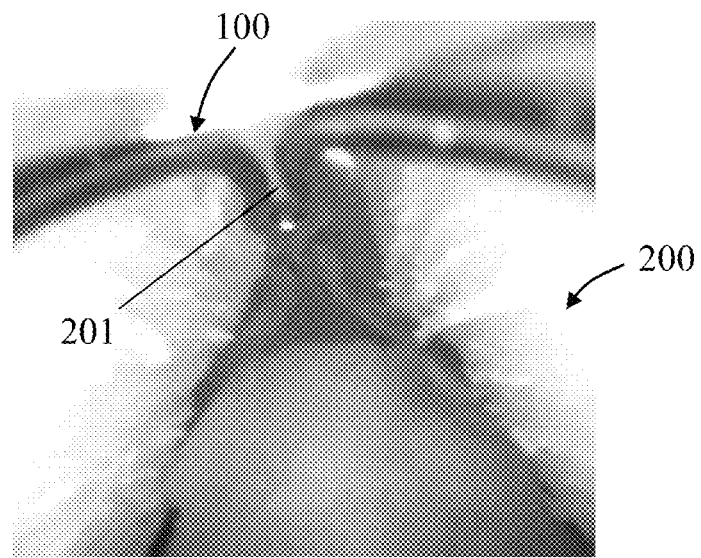
FIG. 2 shows the urological implant of FIG. 1 deployed in a prostatic urethra model, in accordance with some embodiments of the invention.

FIGS. 1E-1F show views of an exemplary urological implant 100 and FIG. 2 shows the urological implant 100 deployed in a prostatic urethra model 200. Urological implant 100 includes:

(1) an elongated body including a spine member 101 having a longitudinal axis X;

(2) a first longitudinal rib 102 and a second longitudinal rib 103 symmetrically opposing each other and connected to elongated body (spine member) 101. First and second longitudinal ribs are elastically shiftable away from each other between a collapsed state (shown in FIG. 3E, for example) and a relaxed state (shown in FIGS. 1E and 1F, for example), relative to spinal longitudinal axis X, in order to retract or/and support periurethral tissue enclosing the prostatic urethra 200; and (3) an implant extraction handle 104 provided proximally distant to spine member 101 (see gap 105) and symmetrically connected at one side 106 thereof to first longitudinal rib 102 and at second side 107 thereof to second longitudinal rib 103.

Implant extraction handle 104 is shaped to correspond an outline of the urological implant 100 formed by the first and second longitudinal ribs 102 and 103 with an extraction handle apex 120 thereof provided adjacent a proximal end 121 of the implant body 101.

Implant extraction handle 104 is configured to shift elastically, when under a pulling force originating therefrom, such that the extraction handle apex 120 points in a proximal direction towards and/or along the longitudinal axis X and away from the implant body to proximal end 121, so as to facilitate and/or force approximation of the first and second longitudinal ribs 102 and 103 relative to longitudinal axis X.

Implant extraction handle 104 is configured to recollapse first and second longitudinal ribs 102 and 103 into the collapsed state, when the urological implant 100 is pulled proximally from implant extraction handle 104 against an edge of a retraction sheath enclosing a lumen sized to accommodate the urological implant therein when in collapsed state (as will be further detailed below in the description relating to FIG. 3).

Each of first and second longitudinal ribs 102 and 103 includes a proximally projecting lateral corner 108 and a distally projecting lateral corner 109, relative to longitudinal axis X. Implant extraction handle 104 is connected to first and second longitudinal ribs 102 and 103 at proximally projecting lateral corners 108 so as to facilitate forcing of the proximally projecting lateral corners 108 to approximate each other when the urological implant 100 is pulled proximally from implant extraction handle 104 against the extraction sheath edge.

Each of first and second longitudinal ribs 102 and 103 is curved and includes a proximal rib end 110 joined to a proximal end 111 of spine member 101, a distal rib end 112 joined to a distal end 113 of spine member 101, and an rib edge portion 114 provided between each pair of corresponding proximal and distal rib ends 110 and 112. Rib edge portion 114 is sized and shaped for positioning in a corresponding posterolateral interlobar groove, when spine member 101 is positioned in and along an anterior interlobar groove 201 in prostatic urethra 200.

Implant extraction handle 104 is shaped to correspond an outline formed by proximal rib ends 110 along a proximal portion 115 of first and second longitudinal ribs 102 and 103.

FIGS. 3A-3F show various scenarios representing stages in an exemplary method of extracting urological implant 100. Urological implant 100 is tethered at a distal portion 116 thereof, using an elastic tether 202, representing and modeling normal machinal resistance exerted from walls of a prostatic urethra during withdrawal of implant 100.

Figure 3A:
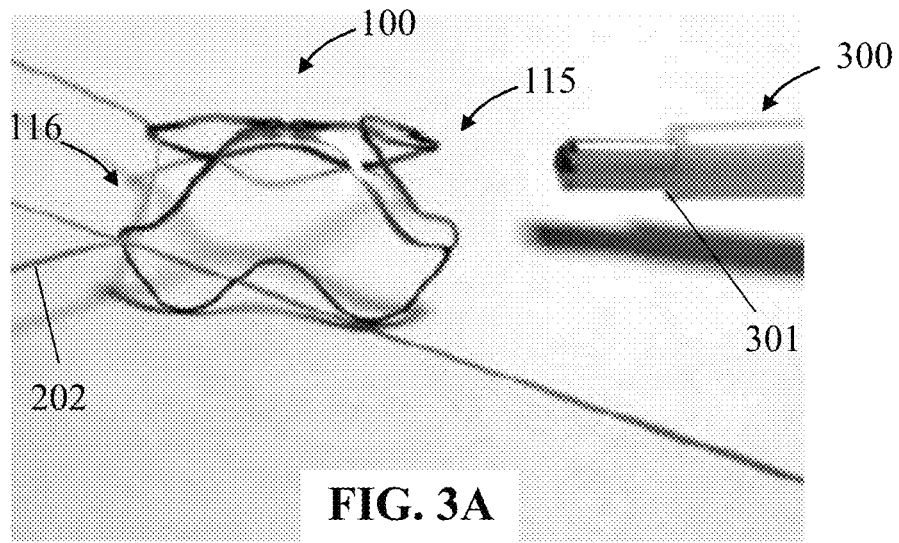
FIGS. 3A-3F show various exemplary scenarios representing stages in an exemplary method of extracting the urological implant of FIG. 1, in accordance with some embodiments of the invention.

FIG. 3A shows positioning an edge 301 of an extraction sheath 300 in proximity to proximal end 115 of urological implant 100, as in case of positioning thereof in the prostatic urethra.

Figure 3B:
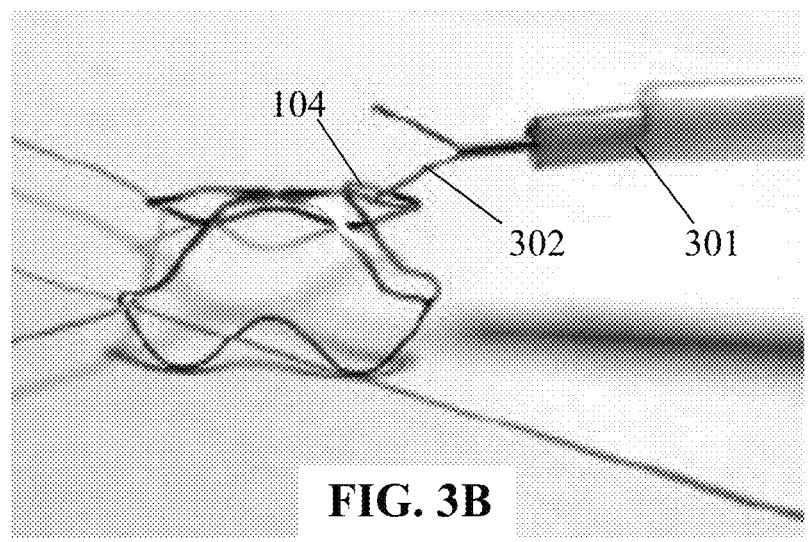

FIG. 3B show applying of a fastening (gripping) device 302 to emerge from extraction sheath 300 distally (simulating emerging into the prostatic urethra).

Figure 3C:
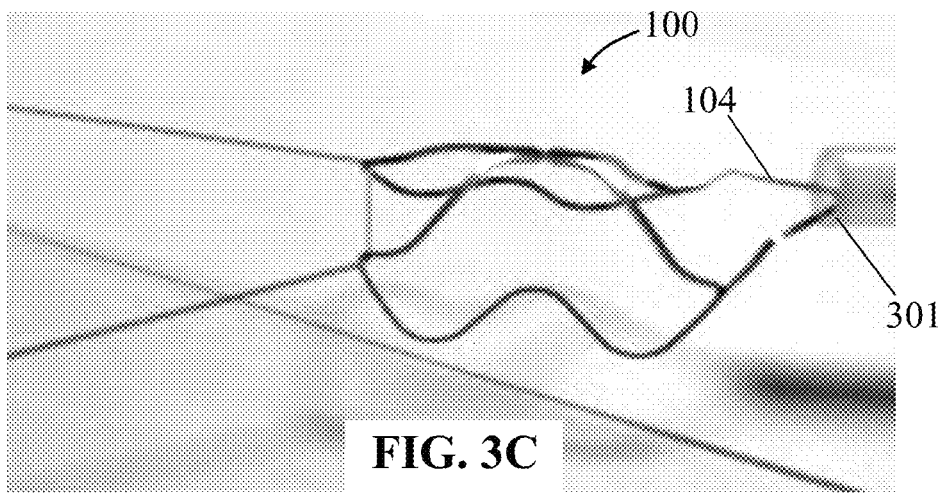

FIG. 3C show fastener 302 gripping (fastening) onto a mid-portion of implant extraction handle 104, and pulling of urological implant 100 proximally from implant extraction handle 104.

Figure 3D:
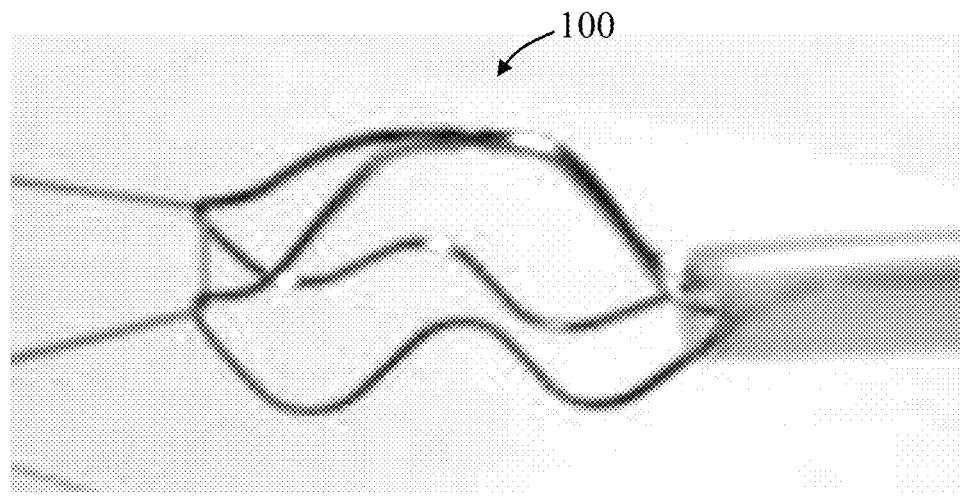
Figure 3E:
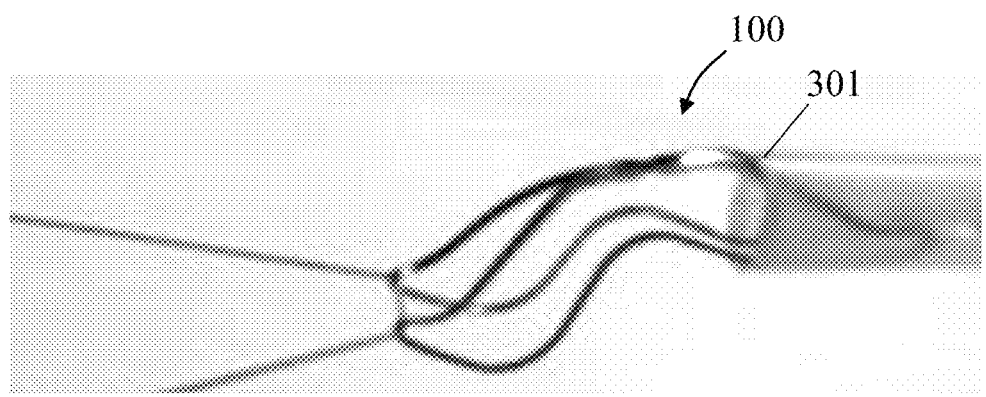
Figure 3F:
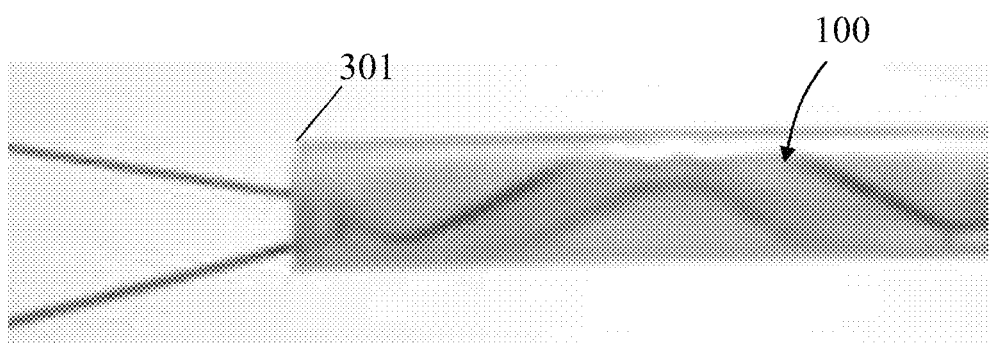

FIG. 3D shows urological implant 100 pulled against edge 301, then it is forced to recollapse (FIG. 3E) until reaching the collapsed state allowing it to be further withdrawn into lumen 303 of extraction sheath 300 (FIG. 3F).

As shown, pulling of urological implant 100 (when under mechanical resistance from prostatic urethra walls, for example) deforms implant extraction handle 104 such that deformation stresses developed thereinside force first and second longitudinal ribs 102 and 103 to approximate one to other until reaching the collapsed state.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

FIGS. 4A-4D schematically illustrate views of an exemplary urological implant 400 having two spaced arches. FIG. 4A shows side view of implant 400 when it is implanted in a portion of the prostatic urethra adjacent to the bladder neck with it cranial end 401 thereof, and in proximity to opening of the ejaculatory duct to the prostatic urethra with caudal end 402 thereof. Implant 400 may be sized to extend along entire length of the prostatic urethra, or only part thereof (for example, extending from a portion adjacently-caudally from the bladder neck, to a portion adjacently-cranially to the opening of the ejaculatory duct. Implant 400 is optionally shaped and configured to be supported against bodily protrusion which constricts the prostatic urethra opening to the bladder neck. Implant 400 includes an elongated implant body 403 having a longitudinal axis 404. Longitudinal axis 404 is perpendicular to a transverse plane 405 and extending between cranial end 401 and caudal end 402 along a median plane 406 dividing implant body 403 into two symmetrical halves.

Implant body 403 includes longitudinally spaced arched members, including a caudal-most arch member 407 and a cranial-most arch member 408, each including an unsupported arch apex 409 located between a first arch end 410 and a second arch end 411, forming together an arched member plane being perpendicular to median plane 406, including a cranial-most arched member plane 412a, formed by arch apex 409 and first and second arch ends 410 and 11 of cranial-most arched member 407, and a caudal-most arched member plane 412b, formed by arch apex 409 and first and second arch ends 410 and 11 of caudal-most arched member 408. Distance between each two closest arch apexes 409 is optionally within a range of 5 mm and 15 mm.

Arched members 407 and 408 are interconnected via arch ends thereof such that first arch ends 410 are connected sequentially along a length of a first longitudinal rib portion 413, and second arch ends 411 are connected sequentially along a length of a second longitudinal rib portion 414. Each of first and second longitudinal rib portions 413 and 414 extends through transverse plane 405.

As illustrated in FIG. 4D, each one of arched members 407 and 408 is elastically bendable so as to facilitate elastic contractibility of implant body 403 when subjected to a transverse compressive force TF crossing median plane 406. Implant body 403 is sized and configured to retract or/and support an anterior portion of the prostatic urethra wall, and allowing collapse of an unsupported posterior portion of the prostatic urethra wall opposing the anterior portion. Optionally and additionally, implant body 403 is sized and configured so as to facilitate physical resistance of the collapsed unsupported posterior portion to a retrograde flow of semen from flowing therethrough towards the bladder neck.

The intersection of transverse plane 405 and a cranial-most arched member plane 412a forms a cranial-most angle β within a range of 20 to 40 degrees. The intersection of transverse plane 405 and caudal-most arched member plane 412b forms a caudal-most angle α within a range of 10 to 50 degrees.

Figure 5A:
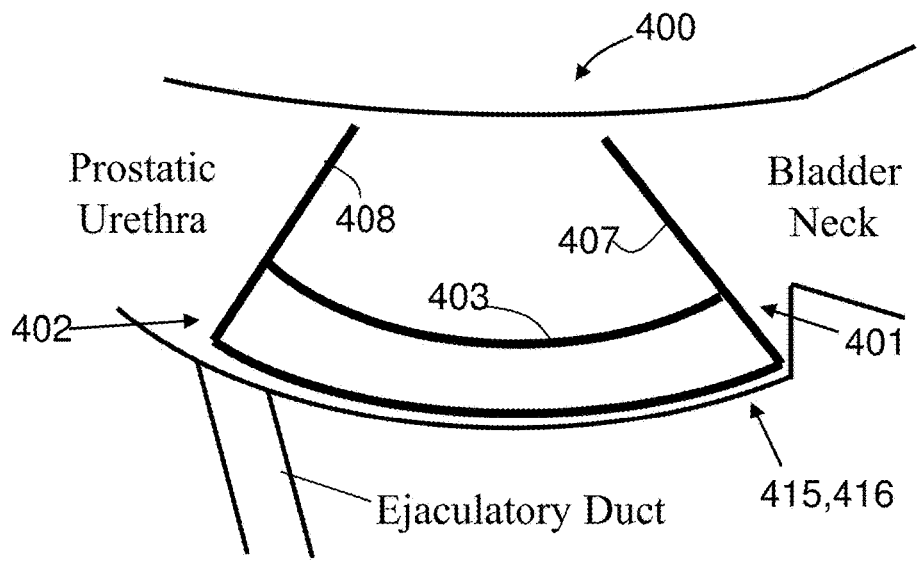
FIGS. 5A-5C schematically illustrate views of an exemplary urological implant having two lateral spacers, in accordance with some embodiments of the invention.
Figure 5B:
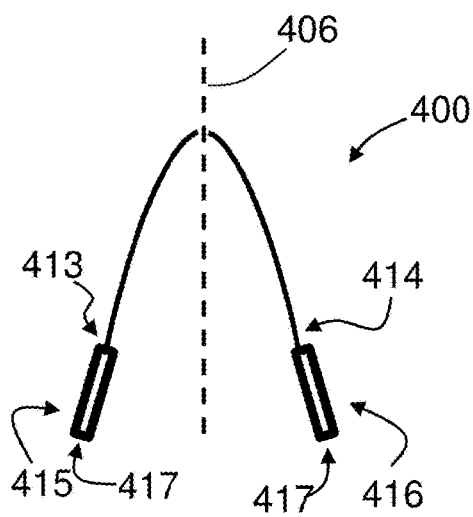
Figure 5C:
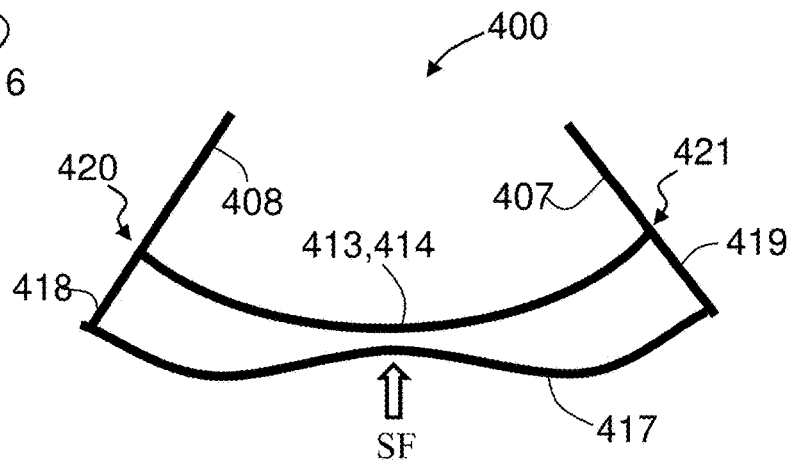

FIGS. 5A-5C schematically illustrate views of an exemplary variation 400' of urological implant 400, which is similar or identical in structure and function to previous variation shown in FIG. 2, but which further includes two lateral spacers—a first lateral spacer 415 emerging from first longitudinal rib portion 413 and a second lateral spacer 416 emerging from second longitudinal rib portion 414. The lateral spacers are independently contractible when subjected to a sagittal compressive force SF parallel to median plane 406.

Each one of the first and second lateral spacers includes a support rib portion 417 curved to resemble curvature of posterior surface of the prostatic urethra. A first of the support rib portions 417 is interconnected with first longitudinal rib portion 413, and a second of support rib portions 417 is interconnected with second longitudinal rib 414, via an at least one support connecting portion including a first support connection portion 418 and a second support connection portion 419. Support rib portion 417 and/or support connecting portions 418 and 419 are elastically bendable so as to facilitate elastic contractibility of lateral spacers 415 and 416, as schematically illustrated in FIG. 5C, which facilitates recoverable approximation support rib portion 417 to a corresponding one of first and second longitudinal rib portions, 413 and 414, when subjected to sagittal compressive force SF.

Each one of first and second lateral spacers 415 and 416 forms a closed figure with first or second support rib portions 417 and first or second longitudinal rib portions, 413 or 414, respectively and first and second support connection portions 418 and 419. The closed figure encloses a contact surface configured for retracting or/and supporting the prostatic urethra wall. Optionally, the closed figure resembles a meniscus lens shape with first and second support rib portions 417 contoured as a convex, and first and second longitudinal rib portions 413 and 414 contoured as a concave, of the meniscus lens shape. The closed figure is formed of a thin strip which incorporates support connecting portions 418 and 419, first or second support rib portion 417 and first or second longitudinal rib portion 413 or 414.

Each one of first and second longitudinal rib portions 413 and 414 forms a first upper corner 420 with first support connecting portion 418 and a second upper corner 421 with second support connecting portion 419, wherein caudal-most arched member 408 extends between respective first upper corners 420, and cranial-most arched member 407 extends between respective second upper corners 421.

FIGS. 6A-6C illustrate views of an exemplary urological implant 500 for retracting or/and supporting a prostatic urethra wall. Implant 500 includes an elongated implant body 501 having a longitudinal axis 502, which is perpendicular to a transverse plane 503 and extends between a cranial end 504 and a caudal end 505 of implant body 501 along a median plane 506 dividing implant body 501 into two symmetrical halves.

Implant body 501 incorporates longitudinally spaced arched members, including a caudal-most arched member 507, a cranial-most arched member 508 and an intermediate arch member 509. Each arched member includes an unsupported arch apex 510 located between a first arch end 511 and a second arch end 512, forming together an arched member plane being perpendicular to median plane 506. Each of the arched members is unsupported or interconnected along its length, including with apex 510, but only via arch ends thereof such that first arch ends 511 are connected sequentially along a length of a first longitudinal rib portion 513, and second arch ends 512 are connected sequentially along a length of a second longitudinal rib portion 514; both first and second longitudinal rib portions 513 and 514 extend through transverse plane 503. The distance between each two closest of arch apexes 510 is within a range of 5 mm and 15 mm.

Each one of arched members 507, 508 and 509 is elastically bendable about longitudinal axis 502 so as to facilitate elastic contractibility of implant body 501 when it is subjected to a transverse compressive force crossing median plane 506. Implant body 501 is sized and configured to retract or/and support an anterior portion of the prostatic urethra wall, thereby allowing collapse of an unsupported posterior portion of the prostatic urethra wall opposing said anterior portion, and to facilitate physical resistance of the collapsed unsupported posterior portion to a retrograde flow of semen from flowing therethrough towards the bladder neck.

The intersection of transverse plane 503 and a cranial-most arched member plane 515, formed by arch apex 510 and first and second arch ends 511 and 512 of cranial-most arched member 508, forms a cranial-most angle β within a range of 20 to 40 degrees. The intersection of transverse plane 503 and a caudal-most arched member plane 516, formed by arch apex 510 and first and second arch ends 511 and 512 of caudal-most arched member 507, forms a caudal-most angle α within a range of 10 to 50 degrees. The arch apex 510 and first and second arch ends 511 and 512 of intermediate arch member 509 forms an intermediate arched member plane being parallel to transverse plane 503.

A first lateral spacer 517 emerges from first longitudinal rib 513 and a second lateral spacer 518 emerges from second longitudinal rib 514, each is individually contractible when subjected to a sagittal compressive force parallel to median plane 506. First and second lateral spacers 517 and 518 are configured to approximate each other towards median plane 506 when arched members are bent about longitudinal axis 502 and implant body 501 is contracted. First lateral spacer 517 includes a first support rib portion 519 interconnected with first longitudinal rib portion 513, and second lateral spacer 518 includes a second support rib portion 520 interconnected with second longitudinal rib 514, via a first support connecting portion 521 and a second support connecting portion and 522. Support rib portions 519 and 520 and/or support connecting portions 521 and 522 are elastically bendable so as to facilitate said elastic contractibility of lateral spacers 517 and 518, wherein elastic contractibility of first and second lateral spacers 517 and 518 facilitates recoverable approximation support rib portion 519 and 520 to a respective (first or second) longitudinal rib portion (513 or 514) when subjected to sagittal compressive force.

Each of first and second lateral spacers 517 and 518 forms a closed figure with its respective support rib portions and longitudinal rib portion, together with first and support connecting portions 521 and 522. The closed figure encloses a contact surface configured for retracting or/and supporting the prostatic urethra wall and resembles a meniscus lens shape with support rib portions 519 and 520 contoured as a convex, and first and second longitudinal rib portions 513 and 514 contoured as a concave, of the meniscus lens shape. The closed figure is formed of a thin strip which incorporates its respective support connecting portions, support rib portion and longitudinal rib portion.

Each one of first and second longitudinal rib portions 513 and 514 forms a first upper corner 523 with first support connecting portion 521 and a second upper corner 524 with second support connecting portion 522. Cranial-most arched member 508 extends between corresponding first upper corner 523, and caudal-most arched member 507 extends between corresponding second upper corner 524.

Arch apex 510 in each arch member is located above, and directed away from, first and second longitudinal rib portions 513 and 514 relative to longitudinal axis 502, such that when the implant supports the prostatic urethra wall, arch apex 510 is located adjacent midline of an anterior portion of the prostatic urethra wall and first and second longitudinal rib portions 513 and 514 are positioned closer to a posterior portion of the prostatic urethra wall.

Implant body 501 has a total height H in an anterior direction within a range of 10 mm to 40 mm and a width W in a lateral direction within a range of 8 mm to 30 mm, when in a relaxed not collapsed configuration (as shown in FIGS. 6A-6C). Arched members form a nominal angle within a range of 0 to 60 degrees along their corresponding arched member plane, when implant body 501 is in a relaxed not collapsed configuration. Implant body 501 is configured to apply a contraction resistive force of at least 100 grf when the arched members are forced into a compressed angle smaller than their nominal angle by at least 20%, thereby retracting or/and supporting the prostatic urethra wall so as to form at a chosen nominal opening size across the prostatic urethra. The chosen nominal opening size has optionally a cross section area of at least 10 mm square.

Implant 500 further includes an implant extraction handle 525 provided caudally distant to implant body 501 and symmetrically connected at one side 526 thereof to first lateral spacer 517 and at a second side 527 thereof to second lateral spacer 518. Implant extraction handle 525 may also be considered a caudal-most arched connection member. Implant extraction handle 525 is shaped to correspond an outline of the urological implant 500 formed by first and second lateral spacers 517 and 518 with an extraction handle apex 528 thereof provided adjacent to arch apex 510 of caudal-most arched member 507, and is configured to shift elastically, when under a pulling force PL (as schematically illustrated in dotted line in FIG. 6B) originating therefrom, such that extraction handle apex 528 points in a caudal direction towards and/or along longitudinal axis 502 and away from arch apex 510 of caudal-most arched member 507.

Implant extraction handle 525 is configured to contract first and second lateral spacers 517 and 518, when the implant 500 is pulled caudally via/from implant extraction handle 525, optionally against a countering surface, such as an edge of a retraction sheath enclosing a lumen sized to accommodate the implant therein when it is in a collapsed state.

Each of first and second support rib portions 519 and 520 forms a lower corner 529 with a respective caudal-most support connection portion 522, wherein implant extraction handle 525 is connected at one side 526 thereof to one of the lower corners 529 at first lateral spacer 517 and at second side 527 thereof to another of the lower corners 529 at second lateral spacer 518.

The present invention further describes a method for supporting or/and extracting a wall of a partially constricted prostatic urethra, by applying urological implant of the present invention such as implant 400 (optionally particularly variation 400' thereof) or implant 500. The method includes at least one of the following steps, not necessarily in same order:

- contracting implant body 401/501 from a relaxed non-contracted configuration by way of elastically bending arched members 407 & 408/507, 508 & 509 and approximating first and second longitudinal rib portions 413 & 414/513 & 514 together.
- positioning implant 400/500 in the partially constricted prostatic urethra with implant body 401/501 contracted into a chosen contracted size and shape configured for atraumatic insertion in the partially constricted prostatic urethra, wherein each arch apex 409/510 is located adjacent midline of an anterior portion of the prostatic urethra wall;
- releasing implant body 401/501 thereby allowing arched members 407 & 408/507, 508 & 509 to autonomously shift first and second longitudinal rib portions 413 & 414/513 & 514 away from each other relative to median plane 406/506, to contact the wall of the partially constricted prostatic urethra and to retract the prostatic urethra by pressing against the prostatic urethra wall. The step of releasing may include retracting or/and supporting an anterior portion of the prostatic urethra wall, and allowing collapse of an unsupported posterior portion of the prostatic urethra wall opposing said anterior portion. The step of releasing may also include allowing the implant body to facilitate physical resistance of the collapsed unsupported posterior portion to a retrograde flow of semen from flowing therethrough towards the bladder neck.

The chosen contracted size is optionally resulted also from elastically bending at least one of support rib portions 417/519 and 520 and support connecting portions 418 & 419/521 & 522 by way of approximating support rib portion to a corresponding first or second longitudinal rib portion, optionally resulted from forces applied to the support rib portion from the prostatic urethra wall during said positioning.

Figure 7:
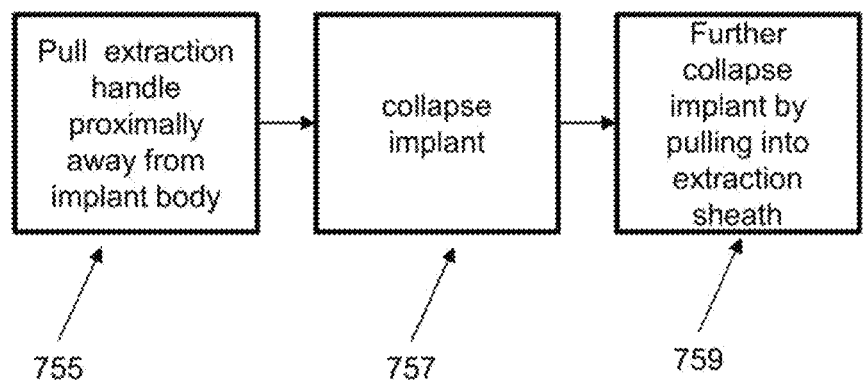
FIG. 7 is a flow chart illustration of method for extracting a urological implant in accordance with an embodiment of the current invention.
Figure 8:
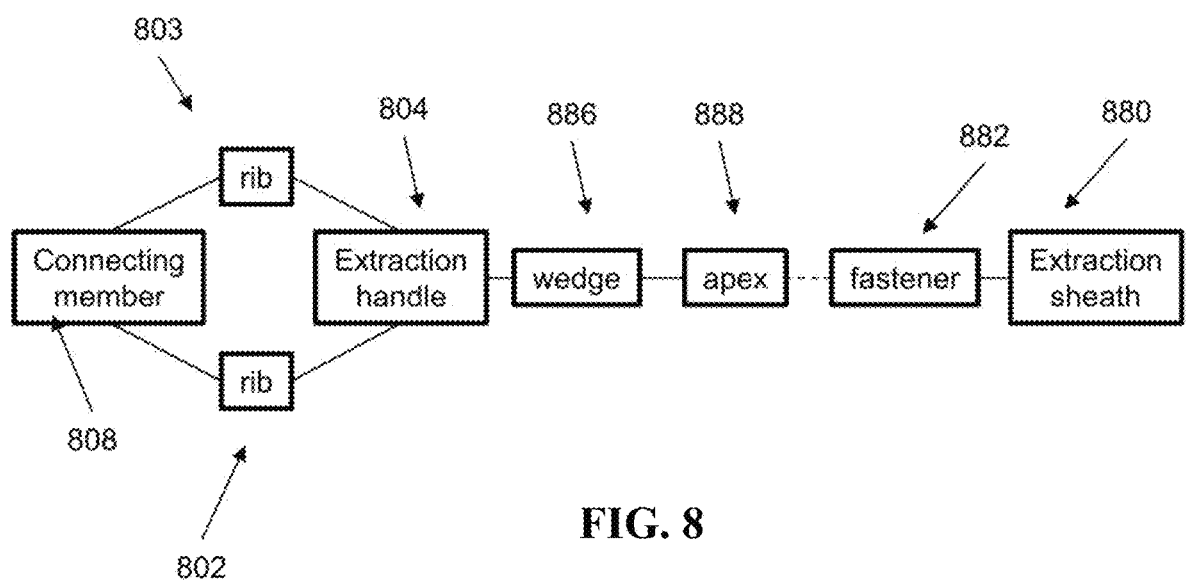
FIG. 8 is a block diagram of a urological implant in accordance with an embodiment of the current invention.

FIG. 7 is a flow chart illustration of method for extracting a urological implant in accordance with an embodiment of the current invention. In some embodiments, a urological implant includes an extraction handle. Optionally, the implant is provided in a relaxed state (for example as illustrated in FIGS. 1E, 1F, 2, 3A, 3B and 8). For example, the implant may be expanded inside a urethra to support periurethral tissue and/or to hold open a urethra. Optionally pulling 755 the extraction handle proximally with respect to the implant body causes the implant to collapse 757 (for example as illustrated in FIGS. 3C and 8). For example, the ribs may collapse 757 approximately towards a longitudinal axis of the device and/or away from the walls of the urethra. In some embodiments, the extraction handle may be pulled 755 by a fastener into a sheath (e.g. a catheter). Optionally, as the device is pulled the extraction handle may take a wedge shape with an apex facing the sheath. For example, as the handle is pulled 755 into the sheath the angled sides of the handle may be pushed together by the inner walls of the sheath further collapsing 759 the handle. Optionally the sides of the handle are connected to the ribs of the implant and/or further collapsing 759 the handle further collapses 757 the ribs of the implant facilitating drawing the implant into the sheath.

FIG. 8 is a block diagram of a urological implant system in accordance with an embodiment of the current invention. In some embodiments, an implant includes a connecting member 808, for example an arch and/or a spine. Optionally, the connecting member 808 connects to one or more longitudinal ribs 802, 803. The ribs 802, 803 optionally spread away from each other (for example laterally away from a longitudinal axis of body) to a support tissue in a urethra. Optionally the ribs 802, 803 and/or the connecting member 808 are attached to an extraction handle 804. For example, the extraction handle 804 may be positioned proximally to the connecting member 808. In some embodiments, when the extraction handle 804 is pulled proximally, ribs 802, 803 contract towards each other (for example laterally towards a longitudinal axis of body). For example, contraction may make it easier to extract the device from a urethra. Optionally, the implant and/or the extraction handle 804 may include a wedge 886 and/or an apex 888. For example, pulling extraction handle 804 and/or the apex 888 proximally positions the apex 888 proximal to the implant. Optionally pulling the implant and/or the extraction handle 804 and/or the apex 888 proximally into an extraction sheath 880 pulls the wedge 886 into the sheath 880. For example, by pulling the wedge 886 into the sheath 880, the walls of the sheath 880 may push inward against the wedge 886 thereby further collapsing the implant laterally inward. For example, the ribs 802, 803 may collapse towards the longitudinal axis of the body 801. For example, a distal end of the sheath 880 may be positioned proximal to the implant and/or a fastener 882 may be passed out a distal end of the extraction sheath 880. Optionally the fastener 882 may be passed through the sheath 880 from a proximal end thereof. The fastener 882 may be fastened to the extraction handle 804 and/or pulled proximally into the extraction sheath 880 to pull the extraction handle 804 and/or collapse the implant and/or draw the wedge 886 into the sheath 880 and/or draw the whole implant into the sheath 880.

Figure 9:
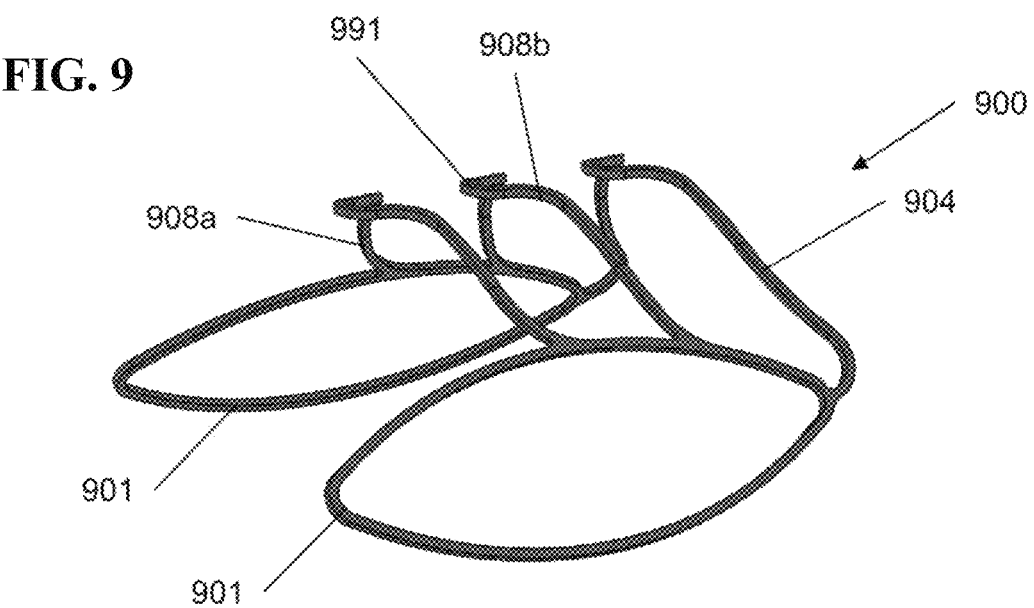
FIG. 9 is a perspective view of a three arched urological implant in an expanded state accordance with an embodiment of the current invention.

FIG. 9 is a perspective view of a three arched urological implant in an expanded state accordance with an embodiment of the current invention. The exemplary device includes three arched members. For example, a proximal most arch includes an extraction handle 904 and/or two distal arches 908a and 908b include connecting members. Optionally, the proximal arch (handle 904) also includes a connecting member. For example, handle 904 and/or connecting members 908a, 908b connect between two longitudinal ribs 901. Optionally, each longitudinal rib 901 may have a closed form. For example, the closed form may include an almond shape (for example with two pointed ends). For example, the almond shape may facilitate collapsing the device. Alternatively or additionally, the closed form may include an oval and/or a rectangle and/or a parallelogram and/or an almond shape with one point and/or a curve (for example, the rib with one or more of the arches may form a wedge shape (e.g. pie shape)) and/or another form. Optionally, the device is biased to the expanded state and/or is relaxed in the expanded state.

In some embodiments, the device is configured to inhibit the device from moving into the bladder. For example, distalmost arch 908a and/or an intermediate arch 908a and/or handle 904 tilts distally. Optionally, when the implant is in place in the prostatic Urethra with the distal end of the device facing the bladder (e.g. the proximal end of the implant facing caudally and/or the distal end facing cranially) the distal tilt of the arches prevents the device from migrating distally towards the bladder. For example, forcing the device distally causes the arches to straighten and/or dig into the wall of the urethra, inhibiting distal migration of the device. Optionally, different connecting members may be inclined in different directions. For example, as illustrated in FIG. 6A a distal connector 508 may be inclined proximally and/or a proximal connector 507 may be inclined distally and/or an intermediate connector 509 may be directed perpendicular to a rib 514.

In some embodiments, a connecting member may include a bend and/or fold (e.g. each of arches 908*a*, 908*b* and handle 904 include a U-shaped fold 991 in its center along the axis of the device). For example, the fold 991 may make the device more flexible and/or facilitate collapsing the device. In some embodiments, the ribs and/or arches are configured to flexible enough to fit into different sized urethras. For example, the almond shape of the ribs and/or the fold 991 of the connecting members may increase the flexibility of the device. For example, a device may be flexible enough to fit in a Urethra having a width of between 6 to 11 mm.

In some embodiments, handle 904 is configured to me more easily bent than one or more of the other arches 908*a*, 908*b*. For example, handle 904 may be made of thinner material (for example between 0 to 10% thinner and/or between 10 to 50% thinner and/or between 50 to 80% thinner, for example the material of the arches may be between 0.4 to 0.6 mm and/or the thickness of the material of the handle may be between 0.2 to 0.4 mm).

In some embodiments, flexibility of a handle may be enhanced by direction of a joint and/or by its curvature. for example, handle 904 is connected to rib 901 with a joint that points approximately proximally and then handle 904 curves distally. For example, at the joint of handle 904 and rib 901, the handle points more distally than the direction a arches 908*a* and 908*b* where they join rib 901. For example, handle 904 include more curvature than arches 908*a* and 908*b*.

Figure 10:
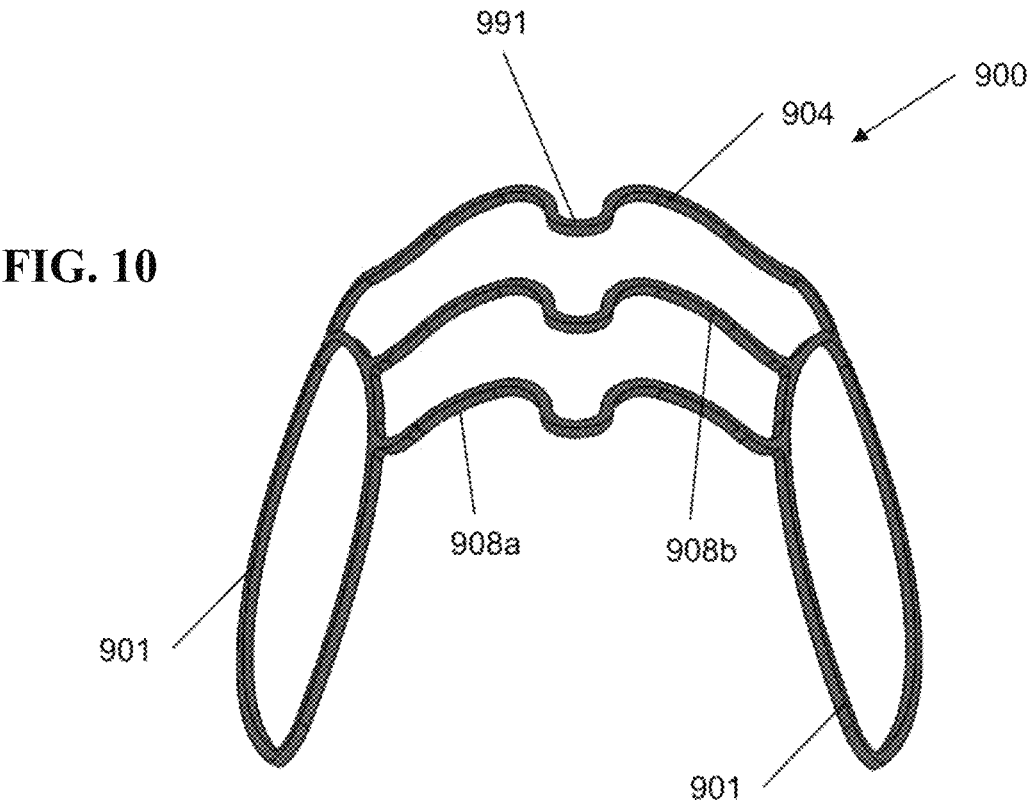
FIG. 10 is a bird's eye view of a three arched urological implant in an expanded state in accordance with an embodiment of the current invention.
Figure 11:
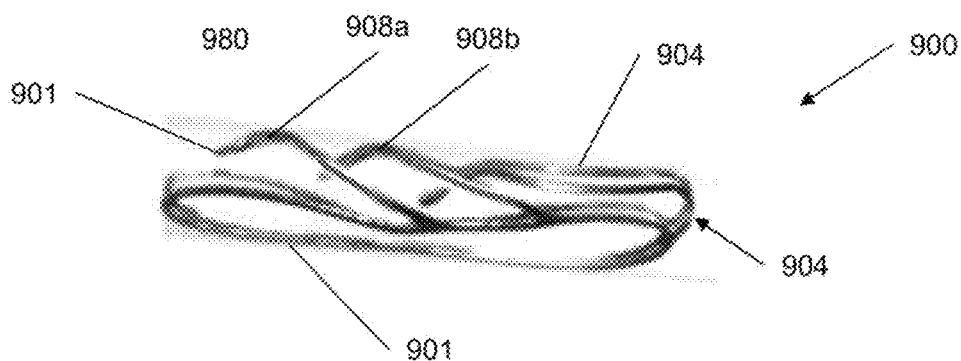
FIG. 11 is a side view of a three arched urological implant in a collapsed state for insertion into a urethra in accordance with an embodiment of the current invention.
Figure 12:
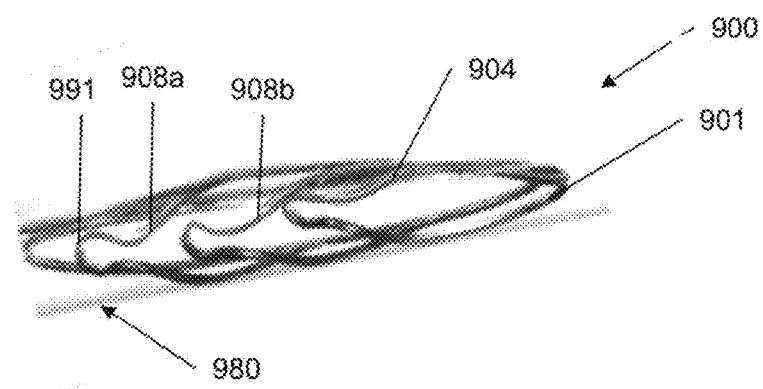
FIG. 12 is a bird's eye view of a three arched urological implant in a collapsed state for insertion into a urethra in accordance with an embodiment of the current invention.

In some embodiments, the distal most connector 908*a* is positions to avoid impinging on a bladder of a subject. For example, connector 908*a* may be connected to a proximal portion of rib 901 (for example distal to 50% of the length of rib 901 and/or body of the device and/or distal to 25% of the length of the device). Optionally, the arches 908*a*, 908*b* and/or handle 904 are configured to remain proximal of the distal end of rib 901 in the expanded configuration (for example as illustrated in FIGS. 9 and 10) and/or in the collapsed configuration (for example as illustrated in FIGS. 11 and 12 and/or as illustrated for example by distal connector 1308*a* of FIG. 13). Alternatively or additionally, a connecting member (e.g. an arch and/or arches) may extend distal to one, some and/or all of the ribs in one or both of the collapsed states (e.g. the collapsed state for insertion and/or the collapsed state for extraction) but not in the expanded state. Alternatively or additionally, in some embodiments, a connecting member may extend distal to one, some or all of the ribs in the expanded state and/or in the expanded and collapsed state.

FIG. 10 is a bird's eye view of a three arched urological implant in an expanded state in accordance with an embodiment of the current invention.

FIG. 11 is a side view of a three arched urological implant in a collapsed state for insertion into a urethra in accordance with an embodiment of the current invention. For example, before insertion into a subject the device is collapsed into an insertion state and inserted into a catheter 980. Optionally, in an insertion configuration handle 904 is folded distally towards the body of the device (e.g. towards ribs 901 and/or arches 908*a*, 908*b*). Optionally, in the insertions configuration handle 904 is folded in the same direction of one, some or all of arches 908*a*, 908*b*.

FIG. 12 is a bird's eye view of a three arched urological implant in a collapsed state for insertion into a urethra in accordance with an embodiment of the current invention.

Figure 13:
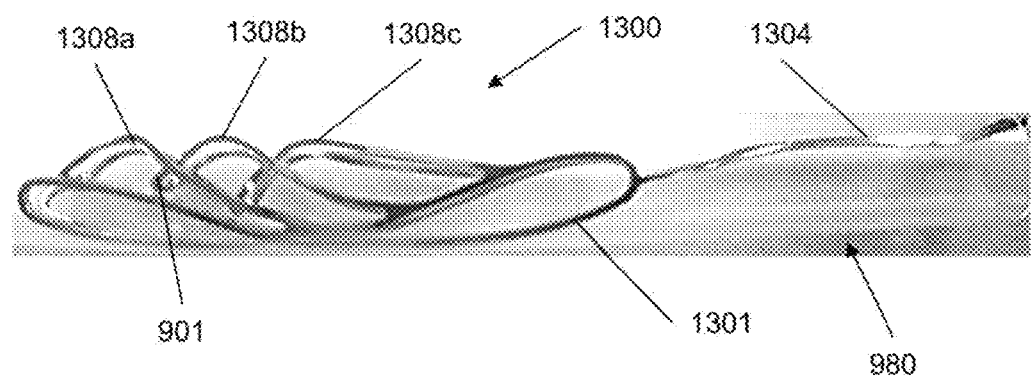
FIG. 13 is a side view of a four arched urological implant 1301 in a collapsed state for extraction from a urethra in accordance with an embodiment of the current invention.

FIG. 13 is a side view of a four arched urological implant 1301 in a collapsed state for extraction from a urethra in accordance with an embodiment of the current invention. For example, when extracting implant 1301, an extraction handle 1304 is pulled proximally. Pulling extraction handle 1304 proximally and/or pulling the device into a sheath 980 optionally causes the implant 1301 to collapse (for example, as described in FIGS. 3A-3F, 7 and 8). Collapsing the implant 1301 optionally facilitates pulling the device into the sheath 980 and/or extracting the device from the Urethra and/or repositioning the device from the Urethra. In some embodiments, in the extraction collapsed state handle 1304 is pulled proximally and/or connecting members (e.g. distal arch 1308*a*, intermediate arch 1308*b* and/or proximal arch 1308*c*) all fold distally and/or the body of the device (for example including rib 1301) collapses inward.

In some embodiments, different sized implants may be available. For example, a four arched implant 1301 may be larger than a three arched implant 901.

FIG. 14 illustrates 4 sizes of implants a large implant 1400*a*, a medium-large implant 1400*b*, a medium implant 1400*c* and a small implant 1400*d* in accordance with embodiments of the current invention. In some embodiments, a larger implant may have more connecting arches than a small implant. For example, large implant 1400*a* includes five arches whereas the medium-large implant 1400*b*, the medium implant 1400*b*, and the small implant 1400*a* each includes four arches. Optionally, proportions of the devices are fixed. For example, the ratio of length to width and/or length to height is approximately the same for each size of the device. Optionally, for each device the height and/or width of the distal side of the device is less than the proximal side.

In many cases, the prostate urethra in grows proportionally in all these dimensions, in This may contrast with other tubular structures (for example some blood vessels). Optionally the urethral implant will have similar proportions, for example, in order to fit snugly in the prostate urethra and/or to be in intimate contact with the prostate urethra mucosa and/or to be covered by it.

Figure 15:
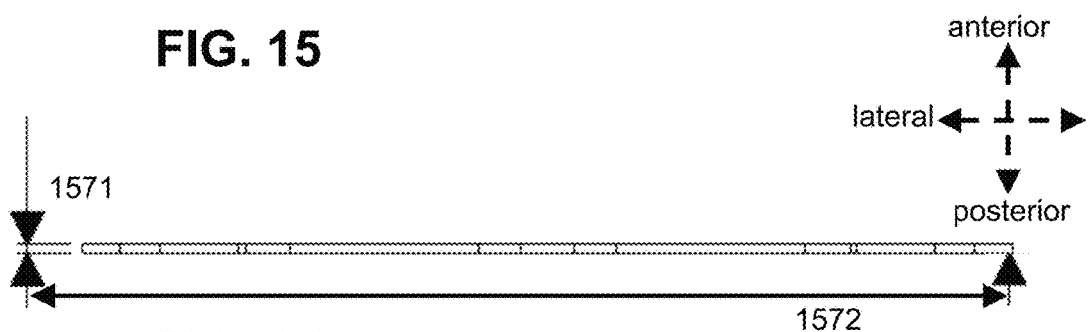
FIG. 15 illustrates a distal (e.g. cranial) end view of a flat implant blank before folding in accordance with an embodiment of the current invention.

FIG. 15 illustrates a distal (e.g. cranial) end view of a flat implant blank before folding in accordance with an embodiment of the current invention. For example, the device may be cut out from a sheet of material. For example, the material may include approximately 0.5 mm thick 1571 nitinol and/or another alloy and/or another material (for example a polymer and/or a composite). Alternatively or additionally, the thickness may range between 0.2 to 1.0 mm and/or between 1 to 3 mm.

Figure 16:
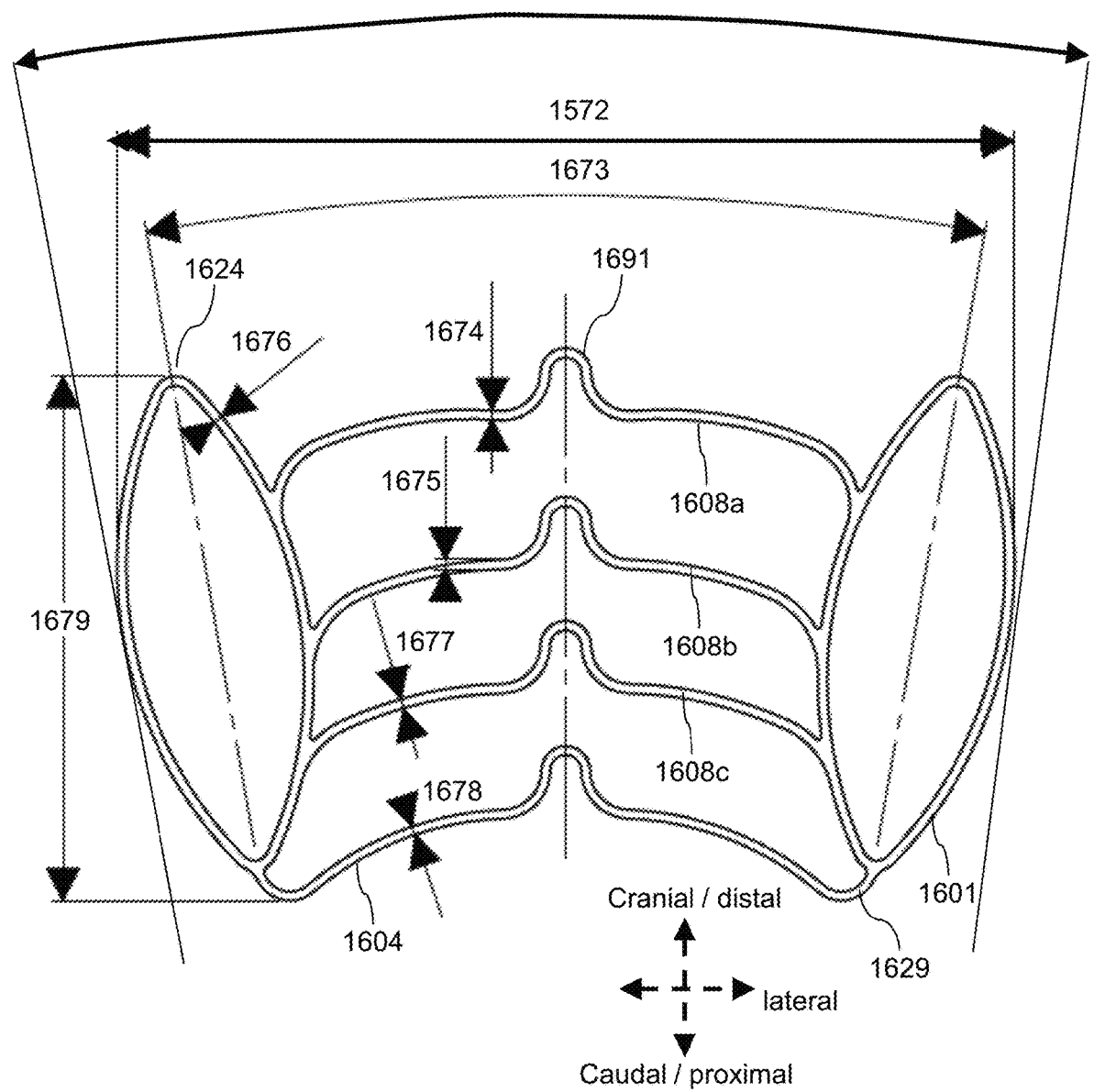
FIG. 16 is an anterior view of a flat implant blank after cutting and/or before folding in accordance with an embodiment of the current invention.

FIG. 16 is an anterior view of a flat implant blank after cutting and/or before folding in accordance with an embodiment of the current invention. The during production of the implant, the structure is optionally cut into the flat blank of material leaving a 2D pattern for example as illustrated in the FIG. 16. For example, the shape may be cut to include two lateral spacers configured as retractors for retracting posterior lateral walls of the prostatic urethra. For example, each retractor may be formed with a closed form having a longitudinal rib 1601. Optionally, the retractors are connected by connecting members 1608a, 1608b and/or 1608c and/or an extraction handle 1604. Optionally extraction handle 1604 is a proximal-most connecting member. For example, the extraction handle 1604 may connect proximal portions of the retractors and/or proximal protrusion (e.g. lower corners 1629) of the implant. Optionally, each retractor includes a distal protrusion (e.g. upper corners 1624). Optionally, some or all of the connecting members 1608a, 1608b, 1608c and/or handle 1604 may include a central apex 1691. For example, the apex 1691 may include a fold in the connecting member 1608a, 1608b, 1608c and/or handle 1604. For example, a central portion of the connecting member may be folded in an anterior and/or cranial direction.

In some embodiments, the parts of the device may be formed of wire like forms. Optionally, the width of the various parts may vary. For example, all or some of all the connecting members 1608a, 1608b, 1608c may have a width 1677, 1675, 1674 that is greater than the width 1678 of handle 1604 device. Optionally, widths 1677, 1675, 1674 of the connecting members 1608a, 1608b, 1608c may vary. For example, the ratio of the width 1678 of the of the handle 1604 (which may be considered the proximal-most connecting member) to the width 1674 of the distal connecting member 1608a may range between 1:1 to 0.9:1 and/or between 0.9:1 to 0.6:1. Optionally, the connecting members may progressively widen as one move distally. For example, the width 1676 of the longitudinal rib 1601 may be approximately equal to the width 1675 of the distal handle 1674.

In some embodiment, in the flattened device, the lateral retractors may open in a distal direction. For example, the angle 1673 between the axes of the opposite lateral retractors may range between 18 to 22 degree and/or between 15 to 18 degrees and/or between 10 to 15 degrees and/or between 22 to 25 degrees and/or between 25 to 30 degrees. For example, the angle 1680 between tangents on lateral edges of the opposite lateral retractors may range between 22 to 28 degree and/or between 15 to 22 degrees and/or between 10 to 15 degrees and/or between 28 to 30 degrees and/or between 30 to 35 degrees.

In some embodiments, the ratio of the length 1679 of the flattened device to its width 1572 may range between 0.54 to 0.6 and/or between 0.4 to 0.54 and/or between 0.6 to 0.7 and/or between 0.2 to 0.4 and/or between 0.7 to 1.0.

FIG. 17 illustrates folding of an implant in accordance with an embodiment of the current invention. For example, the view of FIG. 17 is a cranial orthogonal view. For example, the flat device blank may be folded to an angle 1782 spanning approximately 70 degrees with an apex at the center of the connecting members 1608a, 1608b, 1608c and/or handle 1604. For example, the apex may be rounded for example, by folding over a cylindrical and/or conical jig 1792. For example, the jig may have a radius 1783 of approximately 16 mm. Optionally, the folding will form the connecting members 1608a, 1608b, 1608c and/or handle 1604 into arches for example as illustrated in FIG. 14 and/or FIG. 9.

In some embodiments, after folding, the ratio of the lateral width 1788 between the posterior ends of the retractors 1601 to the average height 1781 of the folded implant (e.g. the average height of the apexes of connecting members 1608a, 1608b, 1608c and extraction handle 1604) may range between 1.2 to 1.6 and/or between 0.8 to 1.2 and/or between 1.6 and 2 and/or between 2 and 3.

FIG. 18A is a lateral orthogonal view of an implant in accordance with In some embodiments of the current invention. For example, the height of the arches (e.g. connecting members 1608a, 1608b, 1608c and/or handle 1604) of the implant may increase as one moves towards the distal end of the device). For example, the highest arch of the implant may be the distal connecting member 1608a and/or the shortest arch may be the proximal handle 1604. For example, the ratio of height 1885 of the highest arch (e.g. rib 1608a) to the height 1886 of the shortest arch (e.g. handle 1604) may range between 1.1:1 to 1.4:1 and/or between 1:1 to 1.1:1 and/or between 1.4:1 to 2:1. In some embodiments, the heights of the arches may decrease approximately linearly from the distal end to the proximal end of the implant.

In some embodiments, the apex 1691 of each arch (for example a fold) is tipped distally. For example, the distally tipped apex 1691 may catch along the anterior side of the urethra and/or prevent cranial migration of the implant in the urethra). For example, the ratio of the height 1886 of an arch (e.g. the handle 1604) with the fold to the height 1887 without the fold may range between 1.02:1 to 1.06:1 and/or between 1:1 to 1.02:1 and/or between 1.06:1 to 1.1:1. In some embodiments, the anterior tip of an arch is distal of the connection between the arch and the retractor. Optionally, an arch (for example, the distal connecting member 1608a from its point of connection with the retractor to its apex 1691) may be angled distally with respect to a longitudinal axis of the retractor at an angle 1889 ranging between 50 to 85 degrees and/or between 30 to 50 degrees. In some embodiments, the ratio of average height 1781 to length 1884 of an implant may range between 0.6 to 0.65 and/or between 0.4 to 0.6 and/or between 0.65 to 0.8 and/or between 0.2 to 0.4 and/or between 0.8 to 1.

In some embodiments, there may be various sizes of implants. Optionally the various sized implants will have some or all of the same relative measurements (for example the ratio of length 1884 to height 1885 of the distal connecting member 1608a and/or handle 1604 etc.). For example, a large implant 1400a may have a length 1884 of approximately 40 mm and/or a medium large implant 1400b may have a length 1884 of approximately 34 mm and/or a medium implant 1400c may have a length 1884 of approximately 30 mm and/or a small implant 1400c may have a length 1884 of approximately 23 mm.

FIG. 18B is a axial view of an implant in accordance with an embodiment of the current invention. Optionally, the body of the implant defined a longitudinal channel 1891 (an exemplary axial projection thereof is illustrated by the dotted area of FIG. 18B). Optionally the channel is open on one side (e.g. the posterior side). For example, the lateral sides of the channel may be determined by lateral retractors 1691 and/or the height of the channel may be determined by the distance from an apex of the lowest connecting member (e.g. handle 1604) to the base of the lateral retractors 1691. Optionally, a lateral axis is defined by and/or parallel to a line 1803 joining cranial protrusions 1624. A median plane 1806 is optionally defined perpendicular to and/or bisecting line 1803. In some embodiments, a line 1803 is not centered along the height (e.g. the anterior-posterior dimension) of channel 1891. For example, along median plane 1806 line 1803 may be in the posterior ½ and/or posterior ⅓ and/or posterior ¼ of the channel. In some embodiments, the channel 1891 is wider on its posterior side than its anterior side. For example, the anterior side of the channel may form an apex. For example, the anterior side of the channel 1891 may for an apex.

In some embodiments, a device will have cranial protrusions 1624 on the posterolateral sides. For example, these protrusions 1624 will impede cranial drift of the implant, for example by resting on a ledge formed near the bladder neck. For example, the lateral distance between the cranial posterolateral will be greater than the lateral extent of the implant on its proximal end. For example, the ratio between the lateral width of the implant at the a caudal end portion to the width between protrusions 1624 may range between 99/100 to 90/100 and/or 90/100 to 80/100 and/or 80/100 to 60/100 and/or between 60/100 to 40/100 and/or between 40/100 to 10/100. For example, the ratio of axial length of the implant to width between the cranial posterolateral protrusions may range between 50/100 to 75/100 and/or 75/100 to 90/100 and/or 90/100 to 1/1 and/or 1/1 to 110/100 and/or 110/100 to 125/100 and/or 125/100 to 150/100 and/or 150/100 to 200/100 and/or 200/100 to 300/100.

In some embodiments, the implant is configured to fit a prostate urethra whose diameter is larger at the cranial side near the bladder neck than at the caudal side near the VERUM MONTANUM or coliculi seminalae.

Figure 19:
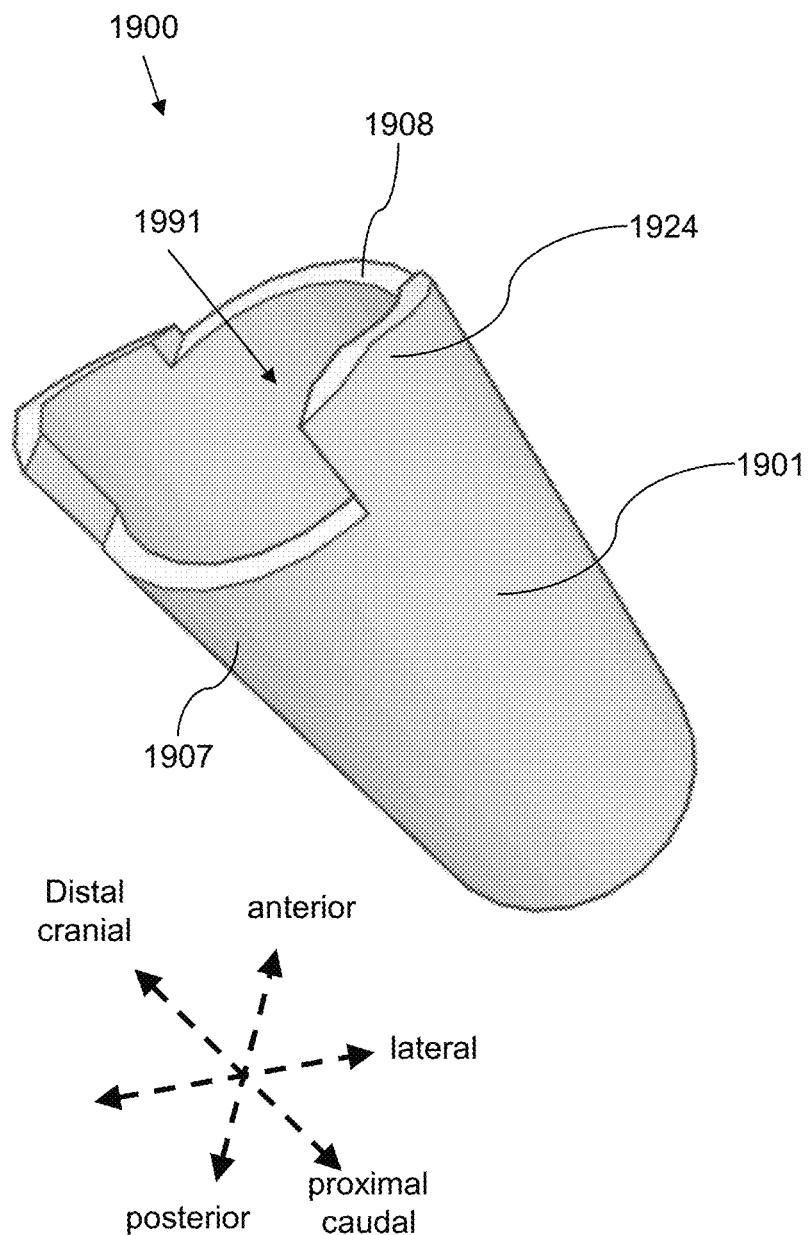
FIG. 19 is a cranial posterior view of a tubular implant in accordance with an embodiment of the current invention.

FIG. 19 is a cranial posterior view of a tubular implant in accordance with an embodiment of the current invention. In some embodiments, the implant may have perforated walls and/or be constructed of a metal and/or wire mesh, for example, similar to a a stent. Alternatively or additionally, the walls of the implant may be solid and/or include a polymer and/or have a covering. In some embodiments, an implant 1900 may have a tubular form. Optionally, posterolateral cranial projections 1924 are included on a cranial/distal end of the device. For example, implant 1900 has the form of a right cylinder with circular cross sections. A closed circular channel 1991 passes through the implant from its caudal end to its cranial end. For example, at point posterior to a central axis of the channel 1991, projections 1924 project cranially surrounding walls of the channel 1991. Optionally, the cranial projections 1924 are positioned on opposite lateral sides of the channel 1991. For example, the protrusions 1924 are configured to rest on the wall of the urethra on opposites sides of a bladder neck and/or outside the bladder and/or on the urethra side of the bladder neck and/or to stretch the bladder neck laterally and/or to for a ledge and/or to rest on a ledge at the bladder neck. For example, this may prevent the implant from migrating cranially through the bladder neck into the bladder. Optionally, the lateral walls of channel 1991 form lateral retractors 1901. For example, the lateral sides may hold open the lateral walls of a prostatic urethra. Optionally, an anterior apex 1908 and/or a posterior wall 1907 of the cylinder form an anterior/posterior retractor. For example, the anterior/posterior retractor may be configured to retract the anterior and/or posterior walls of the urethra. In some embodiments, the implant may collapse and/or expand, for example for insertion into the urethra via a catheter.

Figure 20:
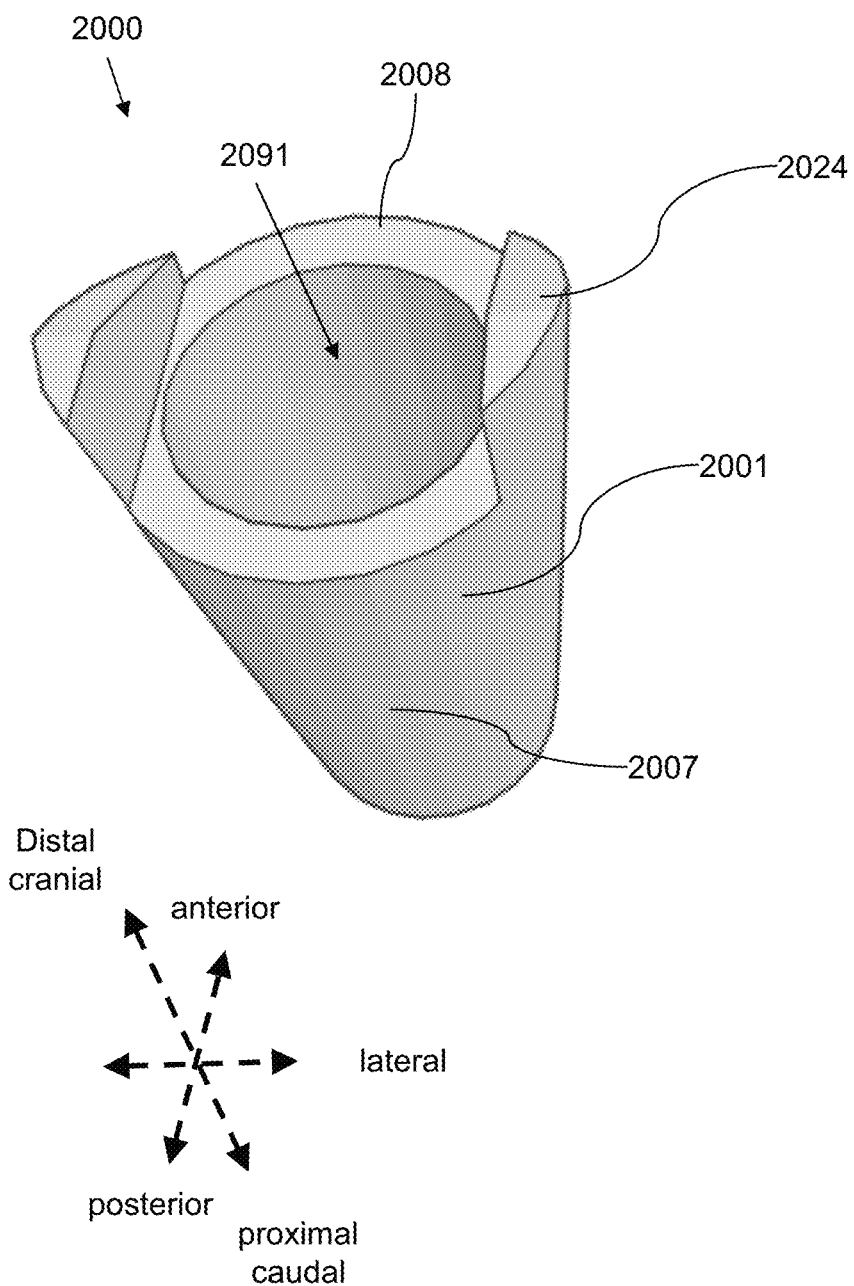
FIG. 20 is a cranial posterior view of a tapered tubular implant in accordance with an embodiment of the current invention.

FIG. 20 is a cranial posterior view of a tubular implant in accordance with an embodiment of the current invention. In some embodiments, an implant 2000 may have a tapered tubular form. In some embodiments, the implant may have perforated walls and/or be constructed of a metal and/or wire mesh, for example, similar to a a stent. Alternatively or additionally, the walls of the implant may be solid and/or include a polymer and/or have a covering. Optionally, posterolateral cranial projections 2024 are included on a cranial/distal end of the device. Optionally, the cranial end of the device is wider than the caudal and and/or the device is tapers caudally. Optionally, the projections 2024 spread cranially. The taper of implant 2000 and/or the cranially spreading of projections 2024 is seen clearly in the orthogonal view of FIG. 23. For example, implant 2000 has the form of a tapered right cylinder with a circular cross section. Alternatively or additionally, an insert may have a different cross section, for example, triangular and/or square etc. A closed circular channel 2091 passes through the implant from its caudal end to its cranial end. For example, at point posterior to a central axis of the channel 2091, projections 2024 project cranially surrounding walls of the channel 2091. Optionally, the cranial projections 2024 are positioned on opposite lateral sides of the channel 2091. For example, the protrusions 2024 are configured to rest on the wall of the urethra on opposites sides of a bladder neck and/or outside the bladder and/or on the urethra side of the bladder neck and/or to stretch the bladder neck laterally and/or to for a ledge and/or to rest on a ledge at the bladder neck. For example, this may prevent the implant from migrating cranially through the bladder neck into the bladder. Optionally, the lateral walls of channel 2091 form lateral retractors 2001. For example, the lateral sides may hold open the lateral walls of a prostatic urethra. Optionally, an anterior apex 2008 and/or a posterior wall 2007 of the cylinder form an anterior/posterior retractor. For example, the anterior/posterior retractor may be configured to retract the anterior and/or posterior walls of the urethra. In some embodiments, the implant may collapse and/or expand, for example for insertion into the urethra via a catheter.

Figure 21:
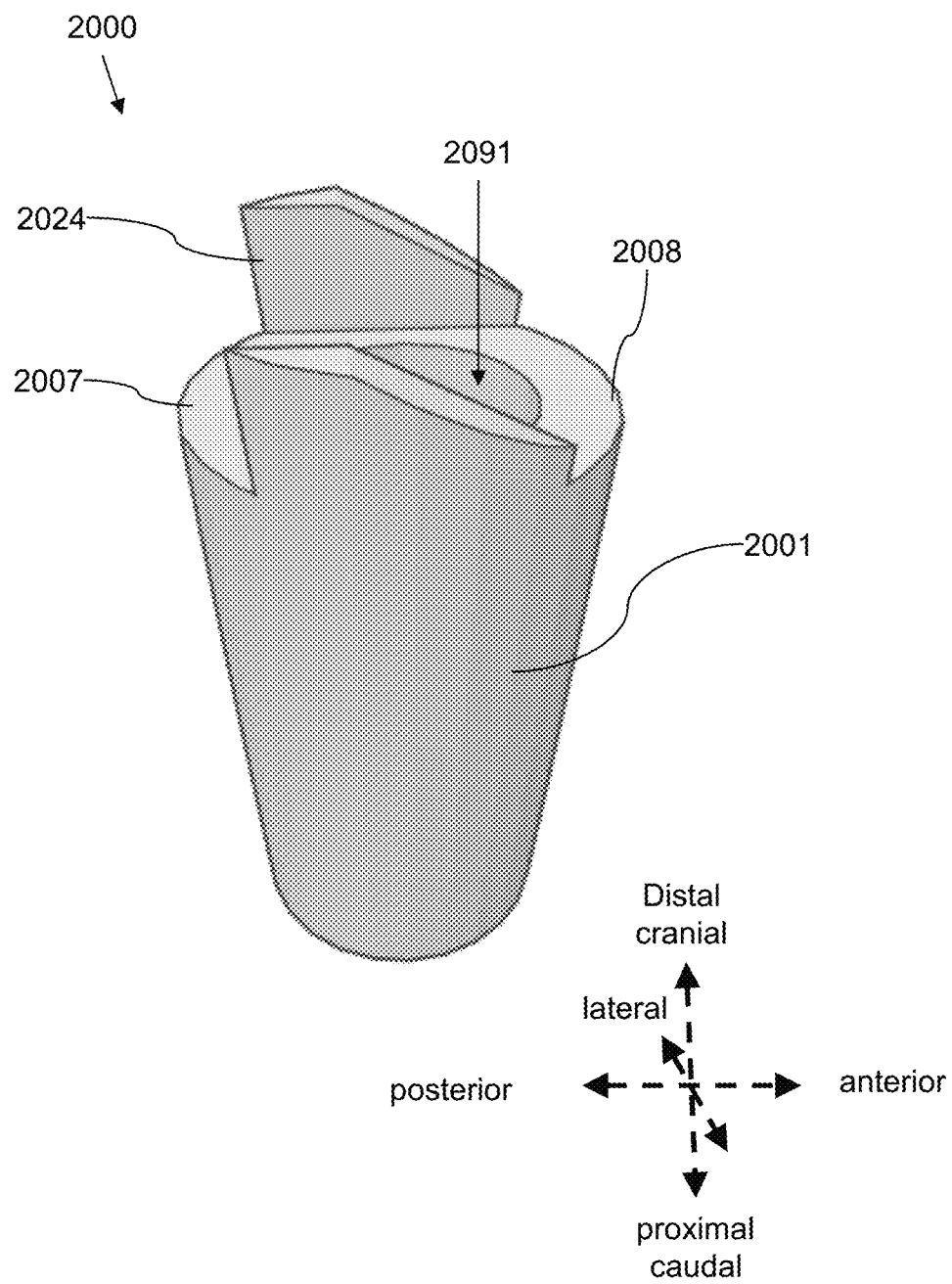
FIG. 21 is a lateral cranial view of a tapered tubular implant in accordance with an embodiment of the current invention.

FIG. 21 is a lateral cranial view of a tapered tubular implant in accordance with an embodiment of the current invention.

FIG. 22 is a posterior cranial view of a tapered tubular implant in accordance with an embodiment of the current invention.

Figure 23:
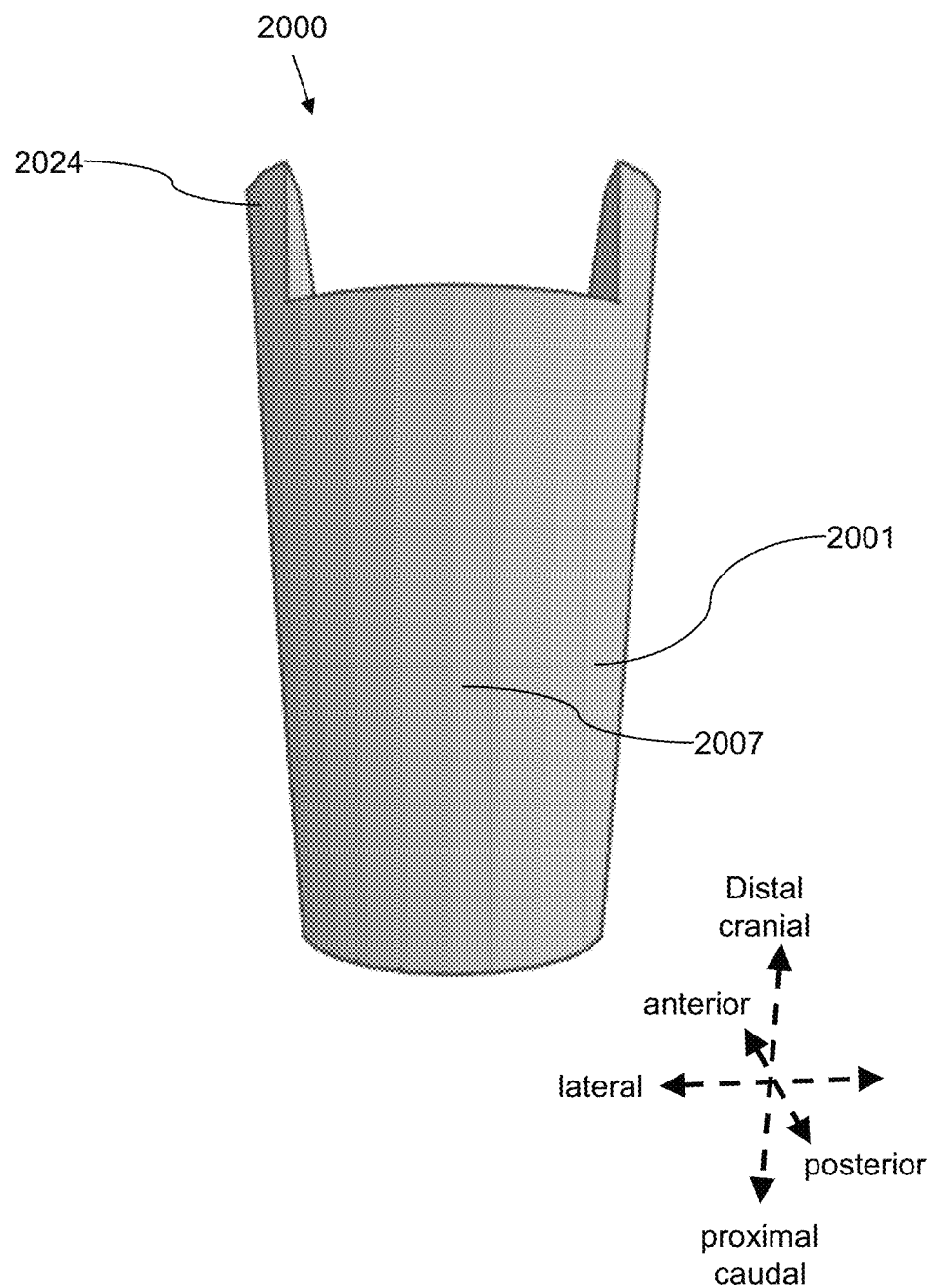
FIG. 23 is a posterior orthogonal view of a tapered tubular implant in accordance with an embodiment of the current invention.

FIG. 23 is a posterior orthogonal view of a tapered tubular implant in accordance with an embodiment of the current invention. The dimensions and/or proportions of the tubular implant 2000 are optionally in the same range as those of the open sided implants described above.

Each of the phrases 'consisting of' and 'consists of', as used herein, means 'including and limited to'. Optionally the extraction handle is on a proximal end thereof and/or proximal of the device.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Throughout this disclosure, the term 'proximal' shall mean a location in a patient's body situated closest to entry point of a medical device or implant, and the term 'distal' shall mean a location in a patient's body situated farthest from such entry point.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about' and approximately as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is of a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. An implant for retracting or/and supporting a prostatic urethra wall, the implant having
    an elongated implant body defining a longitudinal channel having a longitudinal axis, extending between a cranial end and a caudal end of said implant body;
    a pair of cranial projections configured to rest on a ledge of a bladder neck thereby preventing cranial drift of the implant into a bladder;
    a median plane including said longitudinal axis and perpendicular to a line connecting said cranial projections, said median plane having an anterior-posterior axis perpendicular to said longitudinal axis and wherein said line between said pair of cranial projections crosses said channel laterally on a posterior portion thereof posterior to said longitudinal axis,
    a pair of posterolateral retractors located on opposite sides of said median plane and posterior to said axis;
    at least one cranial interconnecting member connecting a cranial portion of each of said pair of posterolateral retractors to a cranial anterior apex located on said median plane anterior to said pair of posterolateral retractors, wherein in an unstressed configuration said at least one cranial interconnecting member extends laterally and posteriorly from said cranial anterior apex to each of said posterolateral retractors;
    at least one caudal interconnecting member connecting a point caudal to said cranial interconnecting member on each of said pair of posterolateral retractors to a caudal anterior apex located on said median plane caudal to said cranial anterior apex and anterior to said pair of posterolateral retractors, wherein in an unstressed configuration said at least one caudal interconnecting member extends laterally and posteriorly from said caudal anterior apex to each of said posterolateral retractors.

2. The implant of claim 1, wherein a lateral width said channel at side line between said pair of cranial projections is greater than a lateral width of said channel at any location anterior thereto.

3. The implant of claim 1, wherein said median plane divides said implant body into two symmetrical lateral halves.

4. The implant of claim 3, further comprising
    wherein one of said pair of cranial projections projects in a cranial direction from each of said posterolateral retractors beyond said cranial interconnecting member.

5. The implant of claim 1, wherein in said unstressed configuration, a lateral width of said implant body between said pair of cranial projections is greater than a lateral width of the implant body between caudal portions of said pair of posterolateral retractors.

6. The implant of claim 1, where a ratio of the a width of the channel between the caudal portions of the pair of posterolateral retractors to the lateral width between the pair of cranial projections ranges between 9/10 to 6/10.

7. The implant of claim 1, wherein a height in an anterior direction of the cranial apex from the cranial portion of the posterolateral retractors is greater than a height in the anterior direction of the caudal apex from caudal portion of the posterolateral retractors.

8. The implant of claim 1, wherein each of said at least one cranial connecting member and said at least one caudal connecting member is elastically bendable so as to facilitate elastic contractibility of said implant body when said implant body is subjected to a transverse compressive force crossing said median plane.

9. The implant of claim 1, wherein a ratio of a length of said implant in a longitudinal direction and an average anterior height of said cranial apex and said caudal apex from said pair of posterolateral retractors ranges between 12/10 to 16/10.

10. The implant of claim 1, further comprising: wherein said at least one caudal connecting member is configured to shift elastically, under a pulling force away from said at least one cranial connecting member to facilitate approximation of said pair of posterolateral retractors relative to said longitudinal axis.

11. The implant of claim 1, wherein said implant body has a total height in an anterior posterior direction within a range of 10 mm to 40 mm and a width in a lateral direction within a range of 8 mm to 30 mm, when in an expanded configuration.

12. The implant of claim 1, wherein a posterior side of the implant body is open.

13. A set of implants for a prostatic urethra comprising:
a large implant having an elongated implant body having a longitudinal axis, said longitudinal axis extends between a cranial end and a caudal end of said implant body along a median plane dividing said implant body into two symmetrical halves said median plane having an anterior-posterior axis perpendicular to said longitudinal axis is perpendicular to a transverse plane and, said transverse plane having lateral axis perpendicular to said an anterior-posterior axis and perpendicular to said longitudinal axis,
posterior to said longitudinal axis,
a pair of posterolateral retractors located on opposite sides of said median plane and posterior to said axis;
at least one cranial interconnecting member connecting a cranial portion of each of said pair of posterolateral retractors to a cranial anterior apex located on said median plane anterior to said pair of posterolateral retractors, wherein in an unstressed configuration said at least one cranial interconnecting member extends laterally and posteriorly from said cranial anterior apex to each of said posterolateral retractors;
at least one caudal interconnecting member connecting a point caudal to said cranial interconnecting member on each of said pair of posterolateral retractors to a caudal anterior apex located on said median plane caudal to said cranial anterior apex and anterior to said pair of posterolateral retractors, wherein in an unstressed configuration said at least one caudal interconnecting member extends laterally and posteriorly from said caudal anterior apex to each of said posterolateral retractors;
a small implant proportionally similar within 10% to said large implant.

14. The set of claim 13, wherein in an unstressed configuration, a lateral width of a cranial end portion of said implant body is greater than a lateral width of a caudal end portion of the implant body.

15. The set of claim 14, where a ratio of the width of a caudal end portion and the lateral width of a cranial end portions ranges between 9/10 to 6/10.

16. The set of claim 13, wherein a height in an anterior direction of a cranial end portion of the implant body is greater than a height in the anterior direction of a caudal end portion of the implant body.

17. The set of claim 16, wherein a ratio the height in the anterior direction of the cranial portion to the height in the anterior direction of the caudal end portion ranges between 11/10 to 14/10.

18. The set of claim 13, wherein each implant body is elastically bendable so as to facilitate elastic contractibility of said implant body when said implant body is subjected to a transverse compressive force crossing said median plane.

19. The set of claim 13, wherein said large implant has a total height in an anterior posterior direction within a range of 30 mm to 40 mm and a width in a lateral direction within a range of 22 mm to 30 mm, when in an expanded configuration and said small implant has a total height in said anterior posterior direction within a range of 10 mm to 13 mm and a width in said lateral direction within a range of 8 mm to 11 mm, when in an expanded configuration.

20. The set of claim 13, wherein a posterior side of the implant body is open.

* * * * *